(12) United States Patent
Choi et al.

(10) Patent No.: US 9,649,350 B2
(45) Date of Patent: May 16, 2017

(54) **USE FOR *DENDROPANAX MORBIFERA* EXTRACT FOR ADJUSTING 15-HYDROXYPROSTAGLANDIN DEHYDROGENASE AND PGE 2 ACTIVITY**

(71) Applicant: INDUSTRY-ACADEMIC COOPERATION FOUNDATION, CHOSUN UNIVERSITY, Gwangju (KR)

(72) Inventors: Cheol-Hee Choi, Gwangju (KR); Hoon Cho, Gwangju (KR); Young-Sook Moon, Gwangju (KR); Ji-Won Han, Gwangju (KR); Ju-Hee Han, Gwangju (KR)

(73) Assignee: Industry-Academic Coorperation Foundation, Chosun University, Gwangju (KR)

( * ) Notice: Subject to any disclaimer, the term of this patent is extended or adjusted under 35 U.S.C. 154(b) by 0 days.

(21) Appl. No.: 14/556,055

(22) Filed: Nov. 28, 2014

(65) Prior Publication Data
US 2015/0202241 A1    Jul. 23, 2015

Related U.S. Application Data

(63) Continuation-in-part of application No. PCT/KR2012/006108, filed on Jul. 31, 2012.

(30) Foreign Application Priority Data

May 30, 2012 (KR) .......................... 10-2012-0057252

(51) Int. Cl.
*A61K 36/25*    (2006.01)
*A23L 33/105*   (2016.01)

(52) U.S. Cl.
CPC ............ *A61K 36/25* (2013.01); *A23L 33/105* (2016.08); *A23V 2002/00* (2013.01)

(58) Field of Classification Search
CPC ....................................................... A61K 36/25
USPC ........................................................ 424/728
See application file for complete search history.

(56) References Cited

FOREIGN PATENT DOCUMENTS

| KR | 10-2004-0097112 | | 11/2004 |
| KR | 10-2004-0107852 | | 12/2004 |
| KR | 10-2011-0078527 | | 7/2011 |
| KR | 20110082292 A | * | 7/2011 |

OTHER PUBLICATIONS

Park et al. "Isolation and anticonmplement activity of compounds from Dendropanax morbifera", Journal of Ethnophamacology 90 (2004) 403-408.*
Lee et al., "Screening of Immune Activation Activities in the Leaves of Dendropanax morbifera Lev.," Korean J. Medicinal Crop Sci., 10(2): 109-115, 2002.
Wu et al., "Synthesis and Biological Evaluation of Novel Thiazolidinedione Analogues as 15-Hydroxyprostaglandin Dehydrogenase Inhibitors," Journal of Medicinal Chemistry, 54: 5260-5264, Jun. 8, 2011.
Choi et al., "Control of the intracellular levels of prostaglandin E2 through inhibition of the 15-hydroxyprostaglandin dehydrogenase for wound healing," Bioorganic & Medicinal Chemistry, 21: 4477-4484, 2013.
Yu et al., "Oleifolioside A, a New Active Compound, Attenuates LPS-Stimulated iNOS and COX-2 Expression through the Downregulation of NF-κB and MAPK Activities in RAW 264.7 Macrophages," Evidence-Based Complementary and Alternative Medicine, 2012.

* cited by examiner

*Primary Examiner* — Chris R Tate
*Assistant Examiner* — Deborah Davis
(74) *Attorney, Agent, or Firm* — Joseph Hyosuk Kim; JHK Law

(57) ABSTRACT

Provided is a 15-PGDH activity adjusting function of a *Dendropanax morbifera* extract. More specifically, since it has been confirmed that the *Dendropanax morbifera* extract has an outstanding effect in suppressing 15-PGDH activity and so increasing $PGE_2$, a composition of the present invention which contains the *Dendropanax morbifera* extract as an active ingredient has the advantage of being able to be used for producing a functional health food and a therapeutic agent for a disease associated with $PGE_2$.

6 Claims, 21 Drawing Sheets

(A) No drug (B) Sucralfate (C) DMHE

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: PGT Sense Primer

<400> SEQUENCE: 1
ggatgctgtt tggaggaatc                                               20

<210> SEQ ID NO 2
<211> LENGTH: 21
<212> TYPE: DNA
<213> ORGANISM: Artificial Sequence

```
<220> FEATURE:
<223> OTHER INFORMATION: PGT Antisense Primer

<400> SEQUENCE: 2
gcacgatcct gtctttgctg a                                              21

<210> SEQ ID NO 3
<211> LENGTH: 20
<212> TYPE: DNA
<213> ORGANISM: Artificial Sequence
<220> FEATURE:
<223> OTHER INFORMATION: MRP4 Sense Primer

<400> SEQUENCE: 3
acctctaacc gacattcctg                                                20

<210> SEQ ID NO 4
<211> LENGTH: 21
<212> TYPE: DNA
<213> ORGANISM: Artificial Sequence
<220> FEATURE:
<223> OTHER INFORMATION: MRP4 Antisense Primer

<400> SEQUENCE: 4
tcaacatatt acagccacca t                                              21

<210> SEQ ID NO 5
<211> LENGTH: 21
<212> TYPE: DNA
<213> ORGANISM: Artificial Sequence
<220> FEATURE:
<223> OTHER INFORMATION: COX 1 Sense Primer

<400> SEQUENCE: 5
cctcatgttt gccttctttg c                                              21

<210> SEQ ID NO 6
<211> LENGTH: 20
<212> TYPE: DNA
<213> ORGANISM: Artificial Sequence
<220> FEATURE:
<223> OTHER INFORMATION: COX 1 Antisense Primer

<400> SEQUENCE: 6
ggcgggtaca tttctccatc                                                20

<210> SEQ ID NO 7
<211> LENGTH: 16
<212> TYPE: DNA
<213> ORGANISM: Artificial Sequence
<220> FEATURE:
<223> OTHER INFORMATION: COX 2 Sense Primer

<400> SEQUENCE: 7
gatctaccct cctcaa                                                    16

<210> SEQ ID NO 8
<211> LENGTH: 17
<212> TYPE: DNA
<213> ORGANISM: Artificial Sequence
<220> FEATURE:
<223> OTHER INFORMATION: COX 2 Antisense Primer

<400> SEQUENCE: 8
gaacaactgc tcatcac                                                   17
```

```
<210> SEQ ID NO 9
<211> LENGTH: 20
<212> TYPE: DNA
<213> ORGANISM: Artificial Sequence
<220> FEATURE:
<223> OTHER INFORMATION: PSA Sense Primer

<400> SEQUENCE: 9
cctcctgaag aatcgattcc                                               20

<210> SEQ ID NO 10
<211> LENGTH: 17
<212> TYPE: DNA
<213> ORGANISM: Artificial Sequence
<220> FEATURE:
<223> OTHER INFORMATION: PSA Antisense Primer

<400> SEQUENCE: 10
gaggtccaac actgaag                                                  17

<210> SEQ ID NO 11
<211> LENGTH: 20
<212> TYPE: DNA
<213> ORGANISM: Artificial Sequence
<220> FEATURE:
<223> OTHER INFORMATION: 15 PGDH Sense Primer

<400> SEQUENCE: 11
tgcttcaaag catggcatag                                               20

<210> SEQ ID NO 12
<211> LENGTH: 20
<212> TYPE: DNA
<213> ORGANISM: Artificial Sequence
<220> FEATURE:
<223> OTHER INFORMATION: 15 PGDH Antisense Primer

<400> SEQUENCE: 12
aacaaagcct ggacaaatgg                                               20

<210> SEQ ID NO 13
<211> LENGTH: 20
<212> TYPE: DNA
<213> ORGANISM: Artificial Sequence
<220> FEATURE:
<223> OTHER INFORMATION: beta actin Sense Primer

<400> SEQUENCE: 13
gactatgact tagttgcgtt                                               20

<210> SEQ ID NO 14
<211> LENGTH: 21
<212> TYPE: DNA
<213> ORGANISM: Artificial Sequence
<220> FEATURE:
<223> OTHER INFORMATION: beta actin Antisense Primer

<400> SEQUENCE: 14
gttgaactct acatacttcc g                                             21
```

USE FOR *DENDROPANAX MORBIFERA* EXTRACT FOR ADJUSTING 15-HYDROXYPROSTAGLANDIN DEHYDROGENASE AND PGE 2 ACTIVITY

TECHNICAL FIELD

The present invention relates to a function of a *Dendropanax morbifera* extract, by which the activities of 15-hydroxyprostaglandin dehydrogenase (15-PGDH) and $PGE_2$ are regulated, and more specifically, it relates to a composition including a *Dendropanax morbifera* extract as an active ingredient, in which the *Dendropanax morbifera* extract allows the activity of 15-PGDH to be inhibited to increase the level of $PGE_2$, thereby preventing and treating the diseases associated with $PGE_2$, or an use thereof.

BACKGROUND ART

*Dendropanax morbifera* Lev., which is a member of a Korea angelica tree, is an evergreen broad-leaved tree that never shed its leaves even during the winter, and grows naturally in the southern coastal area and Jeju-do, Korea, and when the bark of a tree is wounded, a yellow liquid resin is released, and called as Hwangchil (黃漆 a yellow dye).

Hwangchil has been used as a precious paint to give off a golden color for armor, helmet, and other metal jewelry of the emperor since the three kingdoms period and the collection period and intended use of Hwangchil are recorded in "Goryeosa-geolyo (高麗史節要)" of Korea dynasty and "Kye-rim-rye-sa (鷄林類事)", "Kye-rim-ji (鷄林誌)", and "Hae-dong-yeok-sa (海東繹史)" of China and even before that, according to "Chae-bu-won-gu (册府元龜)", "Tong-jeon", and the history books of Tang dynasty, there are records of which Hwangchil was regarded as a specialty of Baekje. In addition, there are some records that Hwangchil trees are effective in alleviation of fever, detoxification of alcohols, and treatment of eye diseases, jaundice, burn, and leprosy and they don't do any harm to human body (Yisijin, Compendium of Materia Medica, China mungwang books, 1590).

The technologies related to the conventional *Dendropanax morbifera* Lev. include Korean Patent Publication No. 2000-0004499, in which a *Dendropanax morbifera* extract with anti-cancer activity is described; Korean Patent Publication No. 2003-0079205, in which a *Dendropanax morbifera* extract, a *Dendropanax morbifera* fraction, and a pharmaceutical composition including them, which are effective in protecting hepatocyte, are described; Korean Patent Publication No. 2004-01077853, in which a *Dendropanax morbifera* extract inhibiting ethanol-induced hepatic damage is described; Korean Patent Publication No. 2004-0107852, in which a *Dendropanax morbifera* extract and fraction that are effective in skin whitening are described; Korean Patent Publication No. 2005-0036093, in which an UV-blocking cosmetic composition including sap of *Dendropanax morbifera* Lev. as an active ingredient is described; and Korean Patent Publication No. 2006-0131360, in which an extract of *Dendropanax morbifera* Lev.'s seeds having outstanding physiological activity is described.

To date, however, neither the molecular mechanisms of a *Dendropanax morbifera* extract involved in regulating the activity of 15-PGDH and $PGE_2$ were identified nor were disease treatments based on such molecular mechanisms reported.

Thus, through a number of experiments, the inventors of the present invention identified that the hexane extract of *Dendropanax morbifera* leaf allows the level of $PGE_2$ to be increased by inhibiting the enzymatic activity of 15-PGDH, and thereby it is effective against diseases associated with $PGE_2$ such as wound and gastric ulcer, and the present invention was completed with the discovery of use of the *Dendropanax morbifera* extract to treat and prevent the diseases associated with $PGE_2$.

DISCLOSURE

Technical Problem

The present invention is based on the molecular mechanism of a *Dendropanax morbifera* extract associated with the activity of 15-PGDH and $PGE_2$, and an object of the present invention is to provide a pharmaceutical composition including a *Dendropanax morbifera* extract as an active ingredient for treating and preventing the diseases associated with the activities of 15-PGDH and $PGE_2$.

Another object of the present invention is to provide a functional composition, for example, food or a cosmetic composition, including a *Dendropanax morbifera* extract and a nutritionally acceptable supplemental food additive for preventing and improving the diseases associated with the activities of 15-PGDH and $PGE_2$.

Technical Solution

In order to achieve the objects above, the present invention provides a pharmaceutical composition including a *Dendropanax morbifera* extract as an active ingredient for treating and preventing the diseases associated with the activities of 15-PGDH or $PGE_2$.

In one exemplary embodiment of the present invention, the above-described *Dendropanax morbifera* extract may be a crude extract of *Dendropanax morbifera* Lev., a polar solvent soluble extract, or a non-polar solvent soluble extract.

In one exemplary embodiment of the present invention, the above-described crude extract of *Dendropanax morbifera* Lev. may be an extract that is soluble in any solvent selected from water including purified water, methanol, ethanol, butanol or a mixed solvent thereof.

In one exemplary embodiment of the present invention, the above-described polar solvent soluble extract may be an extract that is soluble in a solvent selected from water, ethanol, butanol, or a mixed solvent thereof.

In one example of the present invention, the above-described non-polar solvent soluble extract may be an extract that is soluble in hexane, chloroform, dichloromethane or ethyl acetate.

In one exemplary embodiment of the present invention, the above-described pharmaceutical composition may be a pharmaceutical composition effective in (i) inhibiting the enzymatic activity of 15-PGDH; (ii) increasing intracellular and extracellular level of $PGE_2$; (iii) increasing the gene expression of COX-1 (cyclooxygenase-1) and MRP4 (multidrug resistance-associated protein4); (iv) inhibiting the expression of PGT (prostaglandin transporter); and (v) inhibiting the expression of 5α reductase.

In one exemplary embodiment of the present invention, the diseases associated with 15-PGDH activity and $PGE_2$ may be one or more diseases selected from the group consisting of wound, burn, oral ulcer, peptic ulcer and gastric ulcer.

In one exemplary embodiment of the present invention, the above-described wound may be a disease selected from the group consisting of abrasions, lacerations, cuts, incised wound, avulsions, penetrating wound, and skin ulcer.

In addition, the present invention provides a health functional food including a *Dendropanax morbifera* extract as an active ingredient for preventing and improving diseases associated with the activities of 15-PGDH or $PGE_2$.

Advantageous Effects

The *Dendropanax morbifera* extract of the present invention promotes the increase of intracellular and extracellular levels of $PGE_2$ by increasing the gene expression of COX-1 and MRP4 and decreasing the gene expression of PGT, and dual effect can be expected since the decreased gene expression of 5α reductase is led to the quantitative reduction of its target enzyme, 15-PGDH as well as the inhibition of enzymatic activity. Therefore, the composition including the *Dendropanax morbifera* extract according to the present invention can be useful for treating and preventing the diseases associated with the activities of 15-PGDH and $PGE_2$, such as wound, burn, oral ulcer (aphthous ulcer), peptic ulcer (gastric and duodenal ulcer), and gastritis.

MODES OF THE INVENTION

Figure 1:
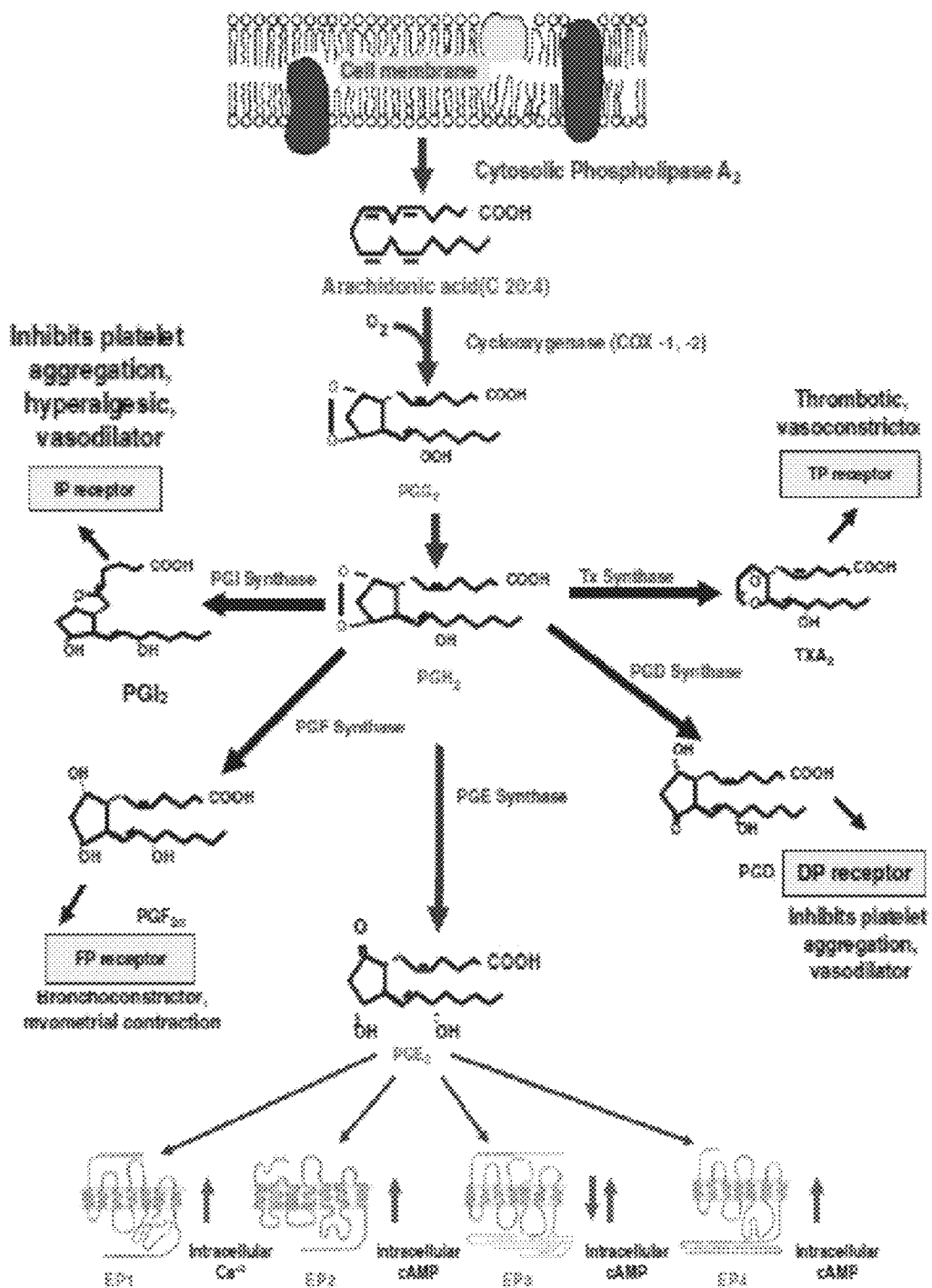
FIG. 1 is a schematic diagram illustrating the process for biosynthesizing a variety of PGs (prostaglandins).
Figure 2:
FIG. 2 illustrates a three dimensional structure of the complex of which 15-PGDH and $PGE_2$ are combined.

Hereinafter, the definitions of terms used in the present invention are described below.

The term, "extract" is a crude extract of *Dendropanax morbifera* Lev., a polar solvent soluble extract, or a non-polar solvent soluble extract.

The term, "crude extract" includes an extract that is soluble in a solvent selected from water including purified water, lower alcohols having 1 to 4 carbon atoms such as methanol, ethanol, and butanol, or a mixed solvent thereof, preferably a soluble in a water and methanol-mixed solvent, and more preferably soluble in 50 to 100% methanol.

The term, "polar solvent soluble extract" includes an extract that is soluble in a solvent selected from water, methanol, butanol or a mixed solvent thereof, preferably soluble in water or methanol, and more preferably soluble in methanol.

The term, "non-polar solvent soluble extract" includes an extract that is soluble in hexane, chloroform, dichloromethane or ethyl acetate, preferably soluble in hexane, dichloromethane or ethyl acetate, and more preferably soluble in hexane or ethyl acetate.

The term, "pharmaceutical composition" means a mixture of the *Dendropanax morbifera* extract of the present invention and other chemical components such as diluent or carrier.

The term, "carrier" is defined as a compound that facilitates the migration of compounds into the cells or tissues. For example, dimethylsulfoxide (DMSO) is a carrier that is commonly used to facilitate the penetration of a number of organic compounds into the cells or tissues of organisms.

The term, "diluent" is defined as a compound that not only stabilizes the biologically active form of target compound, but also a compound that is diluted in water in which it was dissolved. Salts dissolved in buffer solution are used as diluents in the related art. A commonly used buffer solution is phosphate buffered saline solution because it mimics the condition of salts in human solution. Since the buffered salts are able to control the pH of solution at a low concentration, biological activity of compounds are rarely altered by buffer diluents.

The term, "target" or "subject" refers to a random single object requiring treatment including human, cows, dogs, guinea pigs, rabbits, chickens, and insects. Moreover, the target herein includes a random target showing no sign of clinical disease, which participated in the clinical study or a target participated in epidemiological study or a target used as control group.

The term, "tissue or cell sample" refers to a collection of similar cells obtained from the tissues of target or subject. The source of tissue or cell sample may be a fresh, frozen and/or preserved organ or tissue sample or solid tissue from biopsy or aspirate; blood or random components of blood; and the cells from at random point of pregnancy or developmental stage of the target. The tissue sample may also be a primary or cultured cell or cell line.

The term, "effective amount" is the adequate amount that has influence on beneficial or desired clinical or biochemical results. The effective amount can be administered once or more. For the object of the present invention, the effective amount is the amount enough to temporarily relieve, improve, stabilize, reverse, slow or delay the progression of diseased states. If the benefited animals can endure the administration of composition or if it is appropriate to administer the composition to those animals, such composition is regarded as "pharmacologically and physiologically acceptable". If the amount administered is physiologically significant, the formulation is said to be administered in "therapeutically effective amount". If the presence of the formulation caused physiologically detectable changes in subjects, the formulation is physiologically meaningful.

The term, "treating" refers to, unless otherwise stated, reversing, relieving, inhibiting the progression or preventing the disorders, or diseases above, or at least more than one symptom of disorders or diseases above to which the term is applied. As used herein, the term "treatment" refers to the act of treating when "treating" is defined as above.

The term, "functional food" refers to food of which the functionality of the general food is enhanced by addition of the *Dendropanax morbifera* extract of the present invention to the general food. Functionality can be divided into the physical property and the physiological functionality, and the physical property and physiological functionality of the general food will be improved once the extract of the present invention is added to the general food and such food with improved functionality is comprehensively defined as the "functional food" according to the present invention.

Hereinafter, the present invention will be described in detail.

All technical terms used herein, unless otherwise defined, have the same meaning as commonly understood by one of ordinary skill in the related art to which the present invention belongs. Moreover, although desired methods or reagents were stated herein, anything similar or equivalent to these are included in the scope of the present invention. All publications and the contents thereof referenced herein are introduced to the present invention.

The present invention relates to a use of a *Dendropanax morbifera* extract, a particular physiological activity of *Dendropanax morbifera* extract and demonstration thereof.

Figure 3:
FIG. 3 is a photograph of *Dendropanax morbifera* Lev.

*Dendropanox morbifera* LEV., which is a member of a Korea angelica tree, an evergreen broad-leaved tree, is an indigenous species of tree to Korea that grows naturally in Jeju-do and southwestern coastal areas of Korea such as Wan-do, Bogil-do, Haenam and Muan (FIG. 3.). The clove components included in *Dendropanax morbifera* Lev. includes a small amount of terpene and a large amount of sesquiterpene, and despite of differences depending on the collection period or place, germacrene-d, β-selinene, α-amorphene, α-selinene, δ-cadinene, γ-cadinene, T-muurolol, β-elemene, bicyclo[4,4,0]dec-1-en-2-isopropyl-5-methyl-9-methylene, β-cadinene, germacrene-B, α-copaene, α-humulene, and α-cadinene, and a small amount of linalool L, α-terpinene, α-cubebene, α-ylangene, (+)-calarene, 3,7-guaiadine, (−)-isoledene, β-cubebene, limonene, aromadendrene, cadina-1, 4-diene, and the like are included.

Although there is no limitation on the parts of *Dendropanax morbifera* Lev. such as leaf, stem, and bark that can be used for the present invention, it is preferable to use the leaf.

The *Dendropanax morbifera* extract can be produced by methods known in the related art, the modified methods thereof, or the methods of the present invention. As one specific example, it can be produced by the method described below.

The *Dendropanax morbifera* extract or crude extract according to the present invention can be obtained by adding the solvent selected from water including purified water, lower alcohols with 1 to 4 carbon atoms such as methanol, ethanol, and butanol, or a mixed solvent thereof, preferably the mixed solvent of water and ethanol, and more preferably 50 to 100% ethanol, in the volume of about 1 to 30 times, preferably the volume (w/v%) of 5 to 15 times of the weight of *Dendropanax morbifera* Lev.; and then, by extracting at about 0 to 100° C., preferably at room temperature for 10 to 60 hours, preferably by using extraction methods such as cold extraction, hot water extraction, ultrasonic extraction, reflux extraction, or heating extraction for 30 to 50 hours, and preferably by hot water extraction followed by filtering and vacuum evaporation.

Furthermore, the polar or non-polar solvent soluble extract of the present invention can be obtained by dispersing water with a weight by volume of the crude extract obtained by the method described above, preferably by dispersing water with the volume of about 1 to 150 times of the weight of 50 to 100% ethanol crude extract, preferably the volume of 5 to 100 times (w/v%), and then, by adding hexane, ethyl acetate and butanol in order with the volume of about 1 to 10 times of the volume of water, preferably the volume of 1 to 5 times, and fractionating 1 to 5 times, preferably by fractionating 2 to 4 times. Preferably, the hexane extract can be obtained and used.

The concentrate of the above-described extract can be obtained in a type of powder either by lyophilization at −80° C. or vacuum decompression at 50° C.

The present invention includes a method for preparing the *Dendropanax morbifera* extract. The preparing method is no more than one exemplary method thereof, but it can be adequately transformed by a variety of methods based on the technology in the related art and used. For example, an extraction method not exemplified according to the present invention can be successfully conducted by a skilled person in the related art through clear transformation.

For anyone who has common knowledge of the related art to which the present invention belongs, it is possible to find out the detailed reaction condition for preparation of *Dendropanax morbifera* extract of the present invention through the exemplary embodiments described later and thus, detailed description is omitted.

The present invention is based on the discovery of the molecular mechanism by which a *Dendropanax morbifera* extract is associated with the activity of 15-PGDH and $PGE_2$.

The *Dendropanax morbifera* extract of the present invention inhibits the $NAD^+$ dependent activity of 15-PGDH and thereby increases the intracellular and extracellular formation of $PGE_2$.

Prostaglandin (PG) is a mediator known as eicosanoid, which is produced from arachidonic acid released from the cellular membrane by physical, chemical and specific cytokine growth factor stimulation. A variety of biosynthetic processes of PG are illustrated in FIG. 1. Of these, $PGE_2$ is known as an important mediator for wound healing, peptic ulcer, and formation of eyebrow, hair and bone. However, as the $PGE_2$ is rapidly metabolized by $NAD^+$-dependent 15-PGDH, its half life is very short in the body.

In addition, $PGE_2$ is known to act as inflammatory mediator and fibroblast modulator. In order to inhibit severe inflammatory reaction induced by $PGE_2$ such as rheumatic arthritis and osteoarthritis, NSAIDS or COX-2 inhibitors are used to alleviate pain. However, NSAIDS or COX-2 inhibitors result in undesired effects for wound healing because theoretically, the inflammatory reaction is an important stage for wound healing. Therefore, in order to achieve wound healing without formation of keloid, a systematically controlled inflammatory reaction has to take place. According to the recent report, $PGE_2$ inhibits the proliferation of fibroblast and synthesis of collagen and increases the MMPs expression (Yeh et al. 2006). Also, for keloid fibroblasts (KF), formation of $PGE_2$ is less than the fibroblast of control group and moreover, it was reported that antifibrotic effect by $PGE_2$ is recovered if inhibited $PGE_2$ is added externally during the formation of keloid. Thus, if an ingredient with a mechanism that can locally raise the level of $PGE_2$ is used, it has great therapeutic potential for wound healing without leaving a scar.

In this respect, by confirming that the *Dendropanax morbifera* extract of the present invention can effectively inhibit 15-PGDH and has a mechanism involved in $PGE_2$ elevation, and at the same time, through in vitro scratch assay, having confirmed that the *Dendropanax morbifera* extract has effect comparable to that of TGFβ1 in keratinocyte cell migration, despite of some capacity difference (refer to FIGS. 19 to 21), it was identified that it is effective in healing wound rapidly while minimizing the formation of scar.

Additionally, the wound healing effect of the *Dendropanax morbifera* extract of the present invention was confirmed to be equivalent to or better than that of TGFβ1 that was previously known to have an effect of wound healing and TGFβ1 (transforming growth factor β1), as one of the cytokines secreted from a number of different forms of cells (platelet, macrophage, and fibroblast), was discovered in early 1980s for the first time and widely studied in various wound healing models ever since.

As described above, the *Dendropanax morbifera* extract of the present invention possesses an outstanding activity of increasing $PGE_2$ by inhibiting 15-PGDH, and according to one exemplary embodiment of the present invention, the 50% inhibitory effect of *Dendropanax morbifera* leaf extract (methanol, n-hexane, n-butanol, and water) ($ED_{50}$) on enzymatic activity of 15-PGDH was determined to be varying from 1.74 µg/mL to 661.8 µg/mL and particularly, for n-haxane and ethyl acetate extract, $ED_{50}$ were 1.74 µg/mL and 10.6 µg/mL, respectively. Also, in A549 lung cancer cells, the hexane extract of *Dendropanax morbifera* leaf allows the extracellular level of $PGE_2$ to be increased in a concentration dependent manner and in HaCaT cell line, it allows the intracellular and extracellular concentration of $PGE_2$ to be increased.

Figure 5:
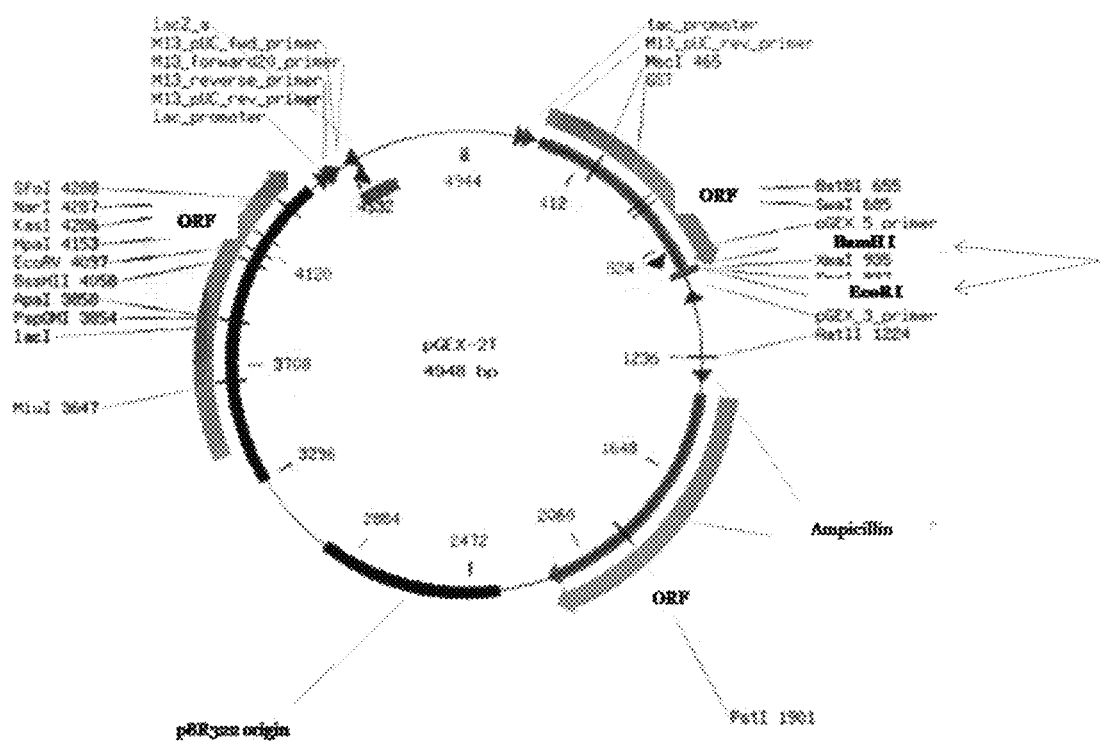
FIG. 5 is a schematic diagram illustrating a PGEX-2T expression vector including recombinant 15-PGDH.

Moreover, the *Dendropanax morbifera* extract of the present invention also affects the expression mechanism of other genes involved in mechanism described in FIG. 5.

In other words, the *Dendropanax morbifera* extract of the present invention allows the mRNA expression of COX-1 (cyclooxygenase-1) and MRP4 (multidrug resistance-associated protein 4) to be increased, and the mRNA expression of PGT (prostaglandin transporter) and 15-PGDH to be decreased.

Especially, through being mediated by $PGE_2$ by the above-described increase of COX-1 expression, the *Dendropanax morbifera* extract provides the healing effect on wound, burn, oral ulcer, peptic ulcer and gastritis.

In one exemplary embodiment of the present invention, through in vitro scratch analysis in HaCaT cell line, it was confirmed that the hexane extract of *Dendropanax morbifera* leaf promoted the wound healing. In addition, these effects were not observed when 15-PGDH and its cofactor $NAD^+$ were co-administered, which indicates that the wound healing effect of *Dendropanax morbifera* extract is mediated by $PGE_2$.

Moreover, controlling the COX-1 expression is more important than controlling the COX-2 expression for the wound healing effect of the *Dendropanax morbifera* extract according to the present invention.

From the exemplary embodiments of the present invention, it can be confirmed that the hexane extract of *Dendropanax morbifera* leaf shows delayed wound healing when SC560, a selective inhibitor of COX-1 and naproxen, a non-selective inhibitor of COX-1/2 are used, and no changes are observed for the wound healing when celecoxib, a COX-2 inhibitor was used.

Moreover, in one exemplary embodiment of the present invention, superior bleeding prevention effect was confirmed in in vivo peptic ulcer model using ICR mice.

Therefore, the *Dendropanax morbifera* extract of the present invention can be useful for preventing and treating the diseases associated with the activities of 15-PGDH and $PGE_2$ based on the molecular mechanism, in which the enzymatic activity and expression of 15-PGDH are inhibited; the intracellular and extracellular concentrations of $PGE_2$ are increased; the gene expressions of COX-1 (cyclooxygenase-1) and MRP4 (multidrug resistance-associated protein4) are increased; the expression of PGT (prostaglandin transporter) is inhibited; and the gene expression of 5α reductase is inhibited and no toxicity was observed for laboratory animals.

The present invention relates to a use of the *Dendropanax morbifera* extract, as an active ingredient, for treating or preventing the diseases associated with the activities of 15-PGDH and $PGE_2$. In more detail, the effect on treating or preventing the diseases, which is defined in the present invention, means to act through the activities of inhibiting the activity of 15-PGDH and increasing the formation of $PGE_2$.

Therefore, "the diseases associated with the activities of 15-PGDH and $PGE_2$" of the present invention particularly refer to the diseases caused by the decrease in $PGE_2$ formation due to increased activity of 15-PGDH, which include wound, burn, oral ulcer, peptic ulcer and gastritis, but the present invention is not limited thereto.

Generally, when the dermis inside of skin is damaged by wound or burn, the level of COX-2 is increased momentarily, and as a result, $PGE_2$ in skin increases and controls the activity of fibroblast contained in the bottom of the wound and during the wound healing process, wound healing is promoted by controlling inflammation, fibrous process.

Thus, the *Dendropanax morbifera* extract of the present invention can exhibit the wound or burn healing effect because it effectively increases $PGE_2$ by inhibiting 15-PGDH.

The above-described "wound" of the present invention is a damaged condition of a body and includes pathological condition wherein tissues constitute the inside of body or outer surface, for instance skin, muscle, nervous tissue, bone, soft tissues, internal organ or blood vessels are separated or destroyed. As the examples of wound, although not limited to these, wound such as contusion or bruise, non-healing traumatic wound, tissue destruction by radiation, abrasion, bone necrosis, laceration, avulsion, penetrated wound, gunshot wound, incised wound, burn, frostbite, skin ulcer, skin dryness, skin keratosis, cracks, burst, dermatitis, pain caused by dermatomyces, surgical wound, vascular disease wound, corneal wound, conditions related to diabetes and poor circulation such as pressure sore, decubitus, and diabetic skin erosion, and chronic ulcer, suture after plastic surgery, spinal damaging wound, gynecological wound, chemical wound and acne are included and damage on some part of an object is included. Preferably, abrasion, laceration, cuts, incised wound, avulsion, penetrated wound and skin ulcer are included.

The "peptic ulcer and gastritis", inflammatory diseases belong to wounds in the broad sense, occur by infection of *Helicobacter pylori* (*Helicobacter pylori*) bacteria which are parasitic on stomach or occur if a balance between the effect of gastric acid and pepsin, which are factors responsible for making stomach wall worn out and the function of mucous membrane (mucosa) that protects the stomach wall is disrupted. In addition, a vast number of drugs including NSAID (non-steroidal anti-inflammatory drug) are accompanied by side effects such as gastrointestinal bleeding for which they are regarded as a major factor causing gastritis and peptic ulcer (gastric ulcer and duodenal ulcer).

Particularly, the wound and peptic ulcer (gastric ulcer and duodenal ulcer) are embodiments of inflammatory diseases, in which the inflammatory diseases refer to pathological conditions resulting from bacterial invasion. As a mediator of inflammation, $PGE_2$ functions as a bioregulator with other prostanoids that are produced by a metabolic pathway of arachidonic acid. Furthermore, endogenous prostaglandin plays an important role in maintaining the integrity of gastrointestinal mucosa and $PGE_2$ is the most effective for this action. The $PGE_2$ indeed protects stomach from reflux esophagitis, alcohol and indomethacin and as the mechanism of action of $PGE_2$, inhibition of gastric contraction, stimulation of bicarbonate secretion from duodenum, secretion of mucus, and secretion of vascular endothelial factor (VEGF, vascular endothelial factor) have been reported (Takeuchi K. Adv Clin Chem. 2010; 51:121-44. Hatazawa, R., et al., Am. J. Physiol Gastrointest Liver Physiol, 2007.293(4) G788-797; Wallace, J. L., Physiol Rev, 2008. 88(4) p. 1547-1565; Gudis, K. and C. Sakamoto, Dig Dis Sci, 2005. 50 Suppl 1, p. S16-23; Miura, S et al., Am J Physiol Gastrointest Liver Physiol, 2004. 287(2) p. G444-451; Araki, H., et al., in rats. Digestion, 2002. 66(3) p. 145-153; Halter, F., et al., Gut, 2001. 49(3) p.443-453).

Moreover, cyclooxygenase (COX), an inflammation inducing enzyme, catalyzes the rate determining step of metabolic action that converts arachidonic acid to prostaglandin $H_2$ ($PGH_2$) and $PGH_2$ further undergo metabolic action and thereby, they are converted to a variety of prostaglandins including $PGE_2$. Therefore, by regulating the expression of $PGH_2$, diseases such as wound, and peptic ulcer (gastric ulcer and duodenal ulcer) can be prevented and treated.

In addition, the composition including the *Dendropanax morbifera* extract as an active ingredient can have effect of oral ulcer prevention and treatment, and this is because $PGE_2$ is known to be effective in preventing and treating the oral mucosa damage cause by aphthous stomatitis or oral ulcer or anticancer drug (Wu-Wang et al., Arch Oral Biol. 1995. 40(12) P1093-1098; Taylor et al., Br Dent J. 1993. 175(4) P125-129; Takaku et al,. Gan To Kagaku Ryoho. 1990 17(11) P2197-2205). Therefore, the *Dendropanax morbifera* extract of the present invention can provide prevention and treatment effect for aphthous stomatitis or oral ulcer or oral mucosa damage caused by anticancer drug, because it efficiently increases $PGE_2$ by inhibiting 15-PGDH.

In one aspect, the present invention relates to a pharmaceutical composition including the *Dendropanax morbifera* extract as an active ingredient to treat and prevent the diseases associated with the activities of 15-PGDH and $PGE_2$. Also in another aspect, the present invention relates to a method, in which the enzymatic activity of 15-PGDH is inhibited by administering the *Dendropanax morbifera* extract to a subject and increases $PGE_2$ formation. In other words, it relates to provide a method for treating and preventing the diseases associated with the activities of 15-PGDH and $PGE_2$ by using the *Dendropanax morbifera* extract.

As used herein, the term "treating", unless otherwise stated, refers to reversing, relieving or inhibiting the progression or preventing diseases or disorders to which the above term is applied or at least one symptom thereof. As used herein, the term "treatment" refers to an act of treating when "treating" is defined as above.

The pharmaceutical composition of the present invention including the *Dendropanax morbifera* extract for preventing and treating the diseases associated with the activity of 15-PGDH includes 0.1 to 50 mass % of the extract with respect to the total weight of the composition.

The pharmaceutical composition including the *Dendropanax morbifera* extract according to the present invention may include adequate carriers, excipients and diluents that are commonly used for preparing the pharmaceutical compositions.

Therefore, the pharmaceutical composition including the *Dendropanax morbifera* extract according to the present invention may be used or formulated in combination with drugs already in use such as steroidal drugs, antihistamines, anti-inflammatory drugs and antibiotics.

The pharmaceutical composition including the *Dendropanax morbifera* extract according to the present invention can be used in different types of oral formulations such as powders, granules, tablets, capsules, suspensions, emulsions, syrups, aerosols, and external application, suppository, and sterilized injection solution each of which by a commonly employed method. In particular, regarding wound healing, it can be made and used in a formulation of external application for skin.

For suitable carriers, excipients, and diluents that can be included in the composition including the extract of the present invention, there are lactose, dextrose, sucrose, sorbitol, mannitol, xylitol, erythritol, maltitol, starch, acacia rubber, alginate, gelatin, calcium, phosphate, calcium silicate, cellulose, methyl cellulose, crude cellulose, polyvinyl pyrrolidone, water, methylhydroxybezoate, propyl hydroxybenzoate, talc, magnesium stearate, and mineral oils.

If it is formulated, normally used diluents or excipients such as filler, extender, binder, humectant, disintegrator, and surfactant are used in preparation.

Solid formulations for oral administration include tablets, pills, powders, granules, and capsules and for these solid formulations are prepared by adding at least one excipient to compound above, for example, starch, and calcium carbonate, sucrose, or lactose, gelatin. Additionally, lubricants such as magnesium steareate, and talc are also used besides simple excipient. As liquid formulations for oral intake, there are suspension, solution, emulsion and syrup and a number of different excipients for example, humectants, sweeteners, aromatics, and preservatives can be included besides water, a simple diluents, and liquid paraffin.

As formulations for parenteral administration, sterilized aqueous solutions, non-aqueous solvents, suspensions, emulsions, lyophilized preparations, and suppositories are included. For non-aqueous solvents and suspensions, vegetable oil such as propylene glycol, polyethylene glycol, and olive oil and injectable ester such as ethyl oleate can be used. Witepsol, macrogol, Tween 61, cacao butter, laurinum, and glycerogelatin can be used as suppository bases.

The used amount of the extract of the present invention varies depending on the age, gender and weight of subject, but 0.0001 to 100 mg/kg, preferably 0.001 to 10 mg/kg can be administered once to several times in a day. Moreover, the dosage can be increased or decreased according to the route of administration, severity of diseases, gender, weight and age. Therefore, the scope of the present invention is not limited at any aspect by the above-described dosage.

The above-described pharmaceutical composition can be administered through a variety of routes to mammals such as mouse, rats, livestock, and human. All methods of administration are predictable, for example, oral, rectal, or intravenous, intramuscular, subcutaneous, intrauterine, or cerebrovascular injection.

The form of pharmacological administration of the pharmaceutical composition of the present invention can be used as pharmacologically acceptable form of salts and also it can be used independently or combined with other pharmacologically active compounds as well as appropriate combination thereof.

Meanwhile, from another perspective, the present invention relates to functional composition including a *Dendropanax morbifera* extract as an active ingredient for the purpose of prevention and improvement of diseases associated with the activity of 15-PGDH. Of these functional compositions, for example, there are health functional foods or cosmetic compositions.

Functionality can be divided into physical properties and physiological properties, and in case some additives are added to the *Dendropanax morbifera* extract of the present invention, physical properties and physiological properties of the composition will be improved.

For instance, by exploiting the molecular mechanism of the *Dendropanax morbifera* extract of the present invention, functional composition for prevention and treatment of disorders such as wound, and gastric ulcer can be prepared.

The *Dendropanax morbifera* extract of the present invention can be used as an active ingredient or additive and supplement to prepare various functional foods and cosmetic products. As one embodiment thereof, the amount of the above-described extract to be added into functional food is normally 0.01 to 15 wt % of the total weight of the composition and besides including the above-described extract, an ordinary skill in the related art may make an appropriate selection and use according to commonly employed methods for preparing food composition or cosmetic composition.

In addition, a number of nutrients, vitamins, minerals (electrolytes) flavorants including natural flavoring agents, coloring agents and enhancement agents peptic acids and its salts, alginic acids and its bases, organic acids, protective colloidal viscosity agents, pH adjusting agents, stabilizers, preservatives, glycerin, and alcohols can be appropriately included.

Since the composition including the *Dendropanax morbifera* extract of the present invention is a natural plant ingredient, it has practically no toxicity and side effects, and thus, it is safe to use for long term for the prevention purpose.

EXAMPLES

Hereinafter, the present invention will be described in more detail with reference to exemplary embodiments. Since these exemplary embodiments are only for illustrating the present invention, it is apparent for one of ordinary skill in the related art that the scope of the present invention is not limited by these exemplary embodiments.

All of the experiments were performed more than 3 times and data was presented as mean±SE. Statistical significance was determined by paired Student's test. $P<0.05$ was considered as statistically significant.

Materials and Instruments

*Dendropanax morbifera* leaves were collected at a Gogwoo farm that is located in Muan of Korea.

PGE2, NAD+, NADH, glutathione-sepharose (glutathione-Sepharose) 4B, DTT(dithiothreitol), SDS (sodium dodecylsulfate), EDTA, reduced glutathione (reduced glutathione), SC560 (COX-1 inhibitor), celexocib (COX-2 inhibitor), naproxen (non-selective COX inhibitor), (5α-dihydrotestosterone (DHT)) mitomycin, sucralfate, CMC (carboxyl methyl cellulose), and minoxidil were purchased from Sigma (St. Louis, Mo., USA) and TGF-β1 was purchased from Biovision Pharmacia Co. (New Jersey, USA).

The cDNA of human 15-PGDH was cloned from human placental cDNA library (Cho and Tai, 2002). UV spectrum was obtained by Shimadzu RF-5301IPC Fluorescence Spectrophotometer (Shimadzu, Japan).

$PGE_2$ enzyme immunoassay kit was purchased from Thermo Scientific (Rockford, Ill, USA) and Real-time PCR was conducted using Light Cycler 2.0 Instrument (Roche, Mannheim, Germany).

The picture of in vitro wound scratch was taken with inverted microscope (Hitachi, Tokyo, Japan).

Analytical HPLC was carried out using Waters SunFire™ (4.6×150 mm, 5 μm) column on Agilent HP1100 series comprising degasser, binary mixing pump, column oven and PDA detector. Using Waters SunFire™ Prep C18 (10×250 mm, and 19×150 mm, 5 μm) column, Semi-preparative HPLC was carried out by Waters multisolvent delivery system combined with DECASSIT™ 6342 degasser. All solvents used in plant extraction were HPLC grade.

Example 1

Preparation of *Dendropanax morbifera* Leaf Extract (1) Preparation of Extract

Collected *D. morbifera* leaves were dried in the shade at room temperature. Dried leaves were extracted with methanol for 3 times. The methanol extracts described above were filtered through Whatman No. 1 filter paper, and combined methanol extracts above described were concentrated in vacuum using rotary evaporator.

Figure 4:
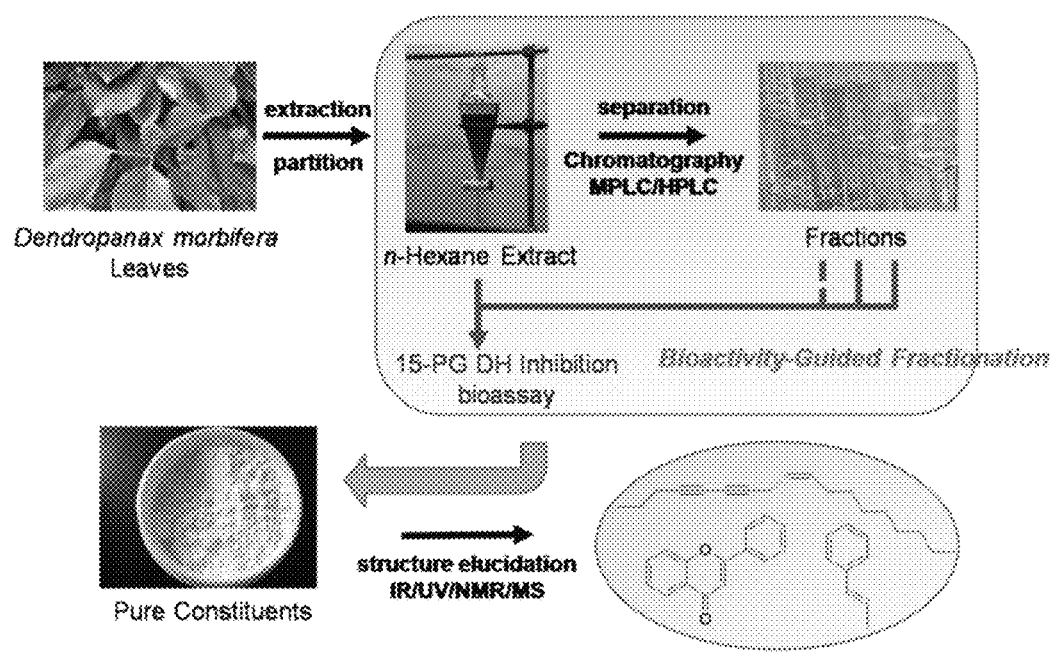
FIG. 4 is a schematic diagram illustrating the process for preparing the *Dendropanax morbifera* extract according to the present invention.

Methanol extracts were suspended in water and then fractionated according to the polarity by hexane, diethyl ether, ethyl acetate, n-butanol and water. Each of the extracts was concentrated using a rotary evaporator. This process is illustrated in FIG. 4.

(2) Fractionation and Separation Process

Using gradient solvent system [$CHCl_3$ (0.1% HCOOH) 100% through $CHCl_3$ (0.1% HCOOH)-MeOH (0.1% HCOOH)/55:45 for 120 min], 10 fractions were provided (DEE01-DEE10) by conducting the activity-guided fractionation under 254 and 280 nm with Isolera Flash Purification system (BIOTAGE, Sweden). Each of the fractions was monitored using HPLC in $MeCN-H_2O$ (0.1% HCOOH) solvent system and each compound was detected.

Furthermore, under UV light (254 nm), spots were detected by a thin layer chromatography or sprayed with vanillin-$H_2SO_4$ and subsequently heated at 110° C.

Using SunFire™ Prep C18 (10×250 mm, and 19×150 mm, 5 μm) column with $MeCN/H_2O$ gradient solvent system including 0.1% formic acid (30:70→100% MeCN), repetitive semi-preparative HPLC experiments were conducted for 40 minutes, and compounds as major ingredients were finally isolated from these fractions.

(3) Results

The yields of *Dendropanax morbifera* extract depending on extraction solvent are listed in Table 1.

TABLE 1

| Sovent | Final Product (g) | Yield (%) |
| --- | --- | --- |
| Methanol | 230.1 | 13.6 |
| n-Hexane | 34.6 | 2.1 |
| Ethyl acetate | 31.0 | 1.9 |
| n-Butanol | 46.6 | 2.8 |
| Water | 98.4 | 5.8 |

Example 2

Identification of 15-PGDH Expression (1) Expression and Purification of 15-PGDH

*Escherichia coli* BL-21 DE3 cells were transformed by a PGEX-2T expression vector including recombinant 15-PGDH between BamH I and EcoR I as illustrated in FIG. 5.

The cells were grown in 500 mL medium containing 50 μg/mL ampicillin at 37° C. and 220 rpm until the O.D. at 600 nm reached 0.6. IPTG (isoprophyl β-D-thiogalactoside, 1M stock solution) was added and the cells were grown for 12 hours at 25° C.

Later, the cells were centrifuged at 4000×g, 4° C. for 30 minutes and collected and the cell pellet was resuspended in 20 mL cold lysis buffer (1× PBS buffer pH 7.4 containing 1 mM EDTA and 0.1 mM DTT) and disrupted by ultrasonication.

The supernatant was slowly applied to glutathione-sepharose 4B column and equilibrated at 4° C. using lysis buffer. The column described above was rinsed with lysis buffer until O.D. at 280 nm was measured lower than 0.005. Then, 15-PGDH was eluted from glutathione-sepharose 4B column by using elution buffer (50 mM Tris-HCl pH 8.0 containing 10 mM reduced glutathione, 1 mM EDTA, and 0.1 mM DTT) for 5 minutes at room temperature.

The concentration of 15-PGDH was measured by a Bradford method (Schleicher and Wieland, 1978) and the purity of 15-PGDH (molecular weight of 29 KD) was identified by SDS-PAGE (sodium dodecyl sulfate polyacrylamide gel electrophoresis) and Coomassie blue staining.

(2) Coomassie Blue Staining

SDS gel was stained with staining solution (0.1% Coomassie brilliant blue R 250, 50% methanol and 10% glacial acetic acid in water) for 20 minutes. The gel described above was washed with destaining solution (10% methanol, 7% glacial acetic acid in water) until the background of gel is completely destained.

(3) Analysis of 15-PGDH Activity

Using fluorescence spectrophotometer, the activity of 15-PGDH inhibitor was analyzed by measuring formation of NADH at 468 nm following excitation at 340 nm.

Figure 6:
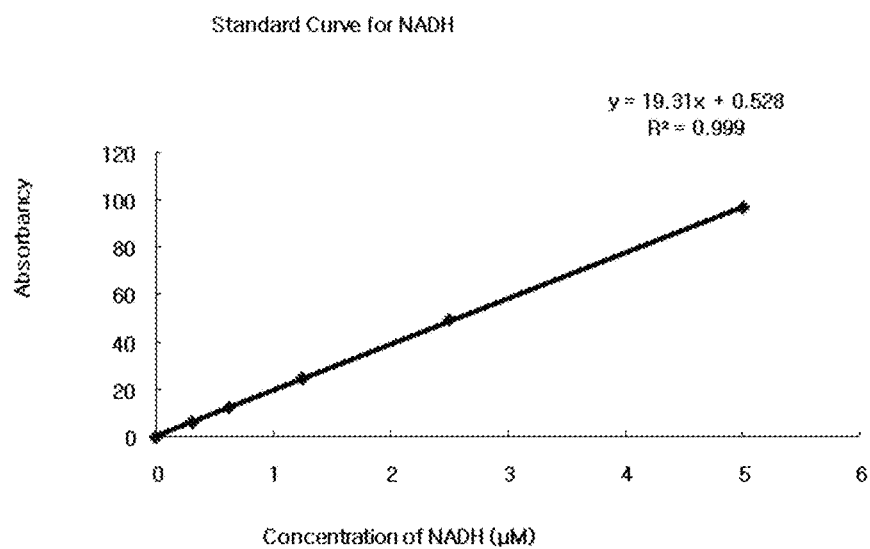
FIG. 6 is a graph illustrating a standard curve of NADH.
Figure 7:
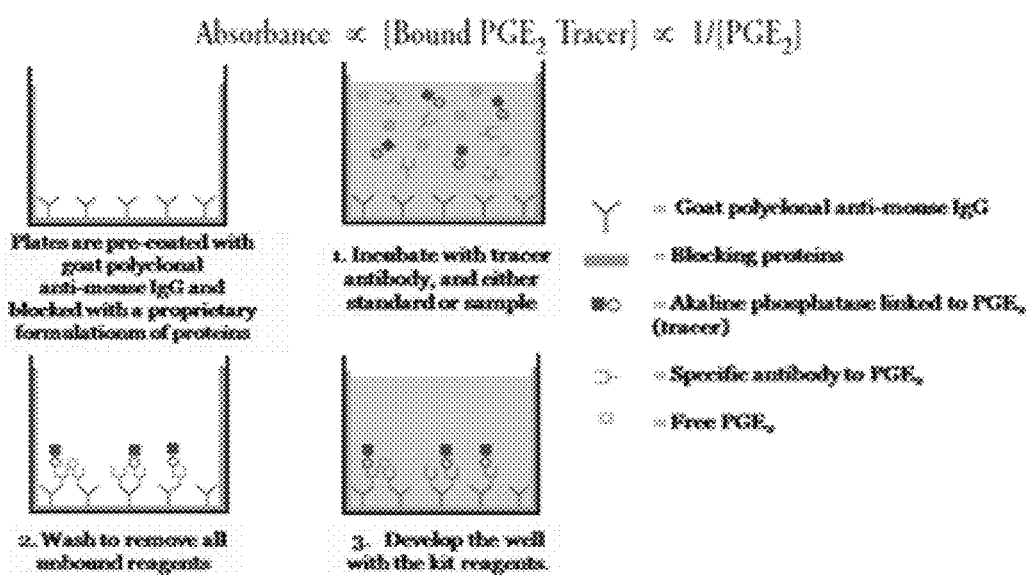
FIG. 7 is a schematic diagram illustrating an experimental procedure using an ELISA kit for the measurement of $PGE_2$.

Tris-HCl buffer (50 mM, pH 7.5) containing 0.1 mM DTT, 0.25 mM NAD+, purified enzyme (10 μg), 21 μM $PGE_2$ and 15-PGDH inhibitors with varying concentrations were added to each of the reaction mixtures. Each of the concentrations was analyzed in triplicate. The absorbance of reaction mixture was calibrated into the activity of 15-PGDH inhibitors from a standard curve of NADH in FIG. 6.

Figure 8:
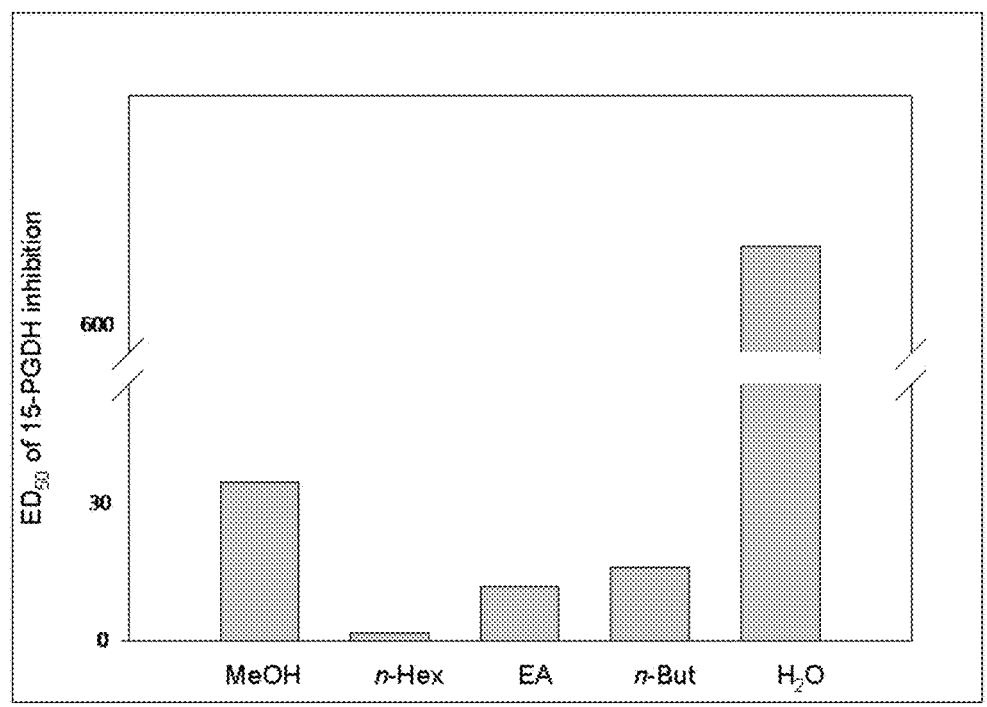
FIG. 8 illustrates a graph showing 15-PGDH inhibitory activity ($ED_{50}$) of Hwangchil (*Dendropanax morbifera*) extract.

The results are listed in Table 2 and illustrated in FIG. 8.

Depending on the extraction solvent, the ED50 of 5-PGDH were determined to be 1.7 μg/mL to 661.8 μg/mL.

TABLE 2

| Extraction solvent | ED50 (μg/mL) |
| --- | --- |
| Methanol | 31.0 |
| n-Hexane | 1.74 |
| Ethylacetate | 10.6 |
| n-Butanol | 14.3 |
| Water | 661.8 |

Example 3

Analysis of Cell Viability (1) Cell Culture

The HaCaT cells, human keratinocyte cell line, were cultured using DMEM (Dulbecco's modified Eagle's media) in 5% $CO_2$ humidified incubator at 37° C.

The A549 cells originated from adenocarcinoma-like human alveolar type II were cultured in RPMI medium, and 5% CO2 humidified incubator at 37° C. And then, LNCaP•FGC (androgen-dependent prostate cancer) cells were cultured in RPMI medium and 5% CO2 humidified incubator at 37° C. All culture media were supplemented with heat-inactivated FBS and 100 μg/mL penicillin (2) Cytotoxicity Test The cytotoxicity was determined by MTT assay (Mosmann, 1983).

Figure 9:
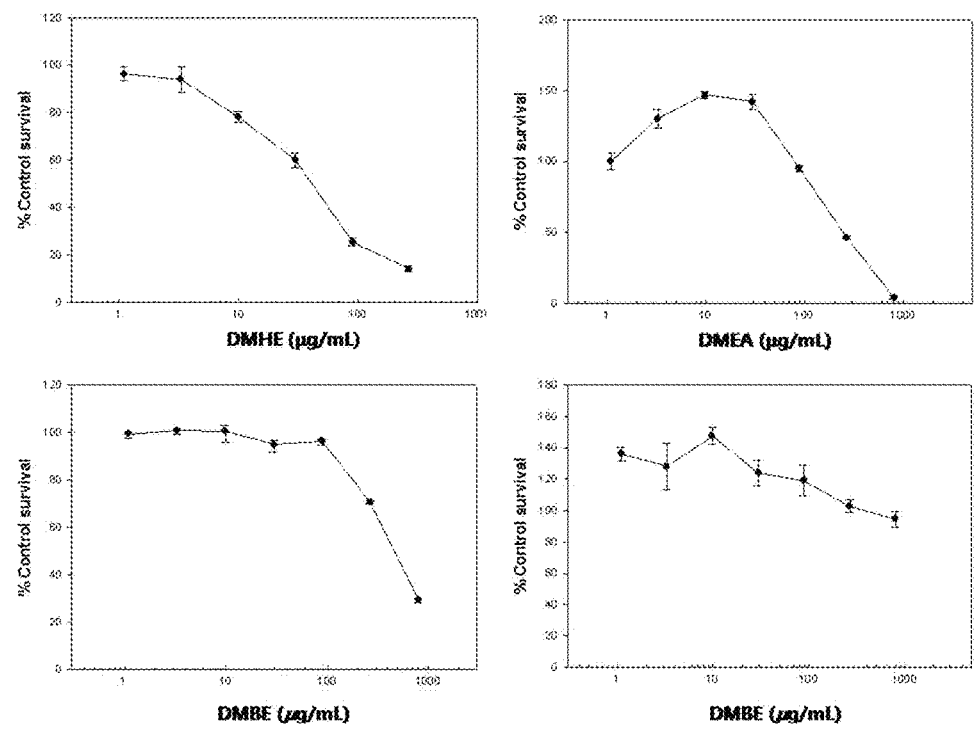
FIG. 9 is a graph illustrating the cytotoxicity assessment of a *Dendropanax morbifera* extract in HaCaT cells by MTT assay.

The HaCaT cells (1×10$^4$/mL) and LNCaP•FGC cells (4×10$^4$/mL) were seeded per 96 μL of DMEM medium on 96-well plate. After overnight culture, drugs were treated for 72 hours and cultured in 10 μL of MTT (5 mg/mL stock solution) for 4 hours. Then, the medium was removed and formazan was dissolved by adding 150 μL of DMSO. Using an ELISA microplate reader (PerkinElmer, California, USA), absorbance at 540 nm was measured. The results are listed in Table 3, and illustrated in FIGS. 9 and 10.

TABLE 3

| Solvent | HaCaT IC$_{50}$ (μg/mL) | LNCaP•FGC IC$_{50}$ (μg/mL) |
|---|---|---|
| n-Hexane | 39.86 | 169 |
| Ethyl acetate | 246.27 | 88.3 |
| n-Butanol | 471.40 | 562 |
| Water | >1000.00 | >800 |

Figure 10:
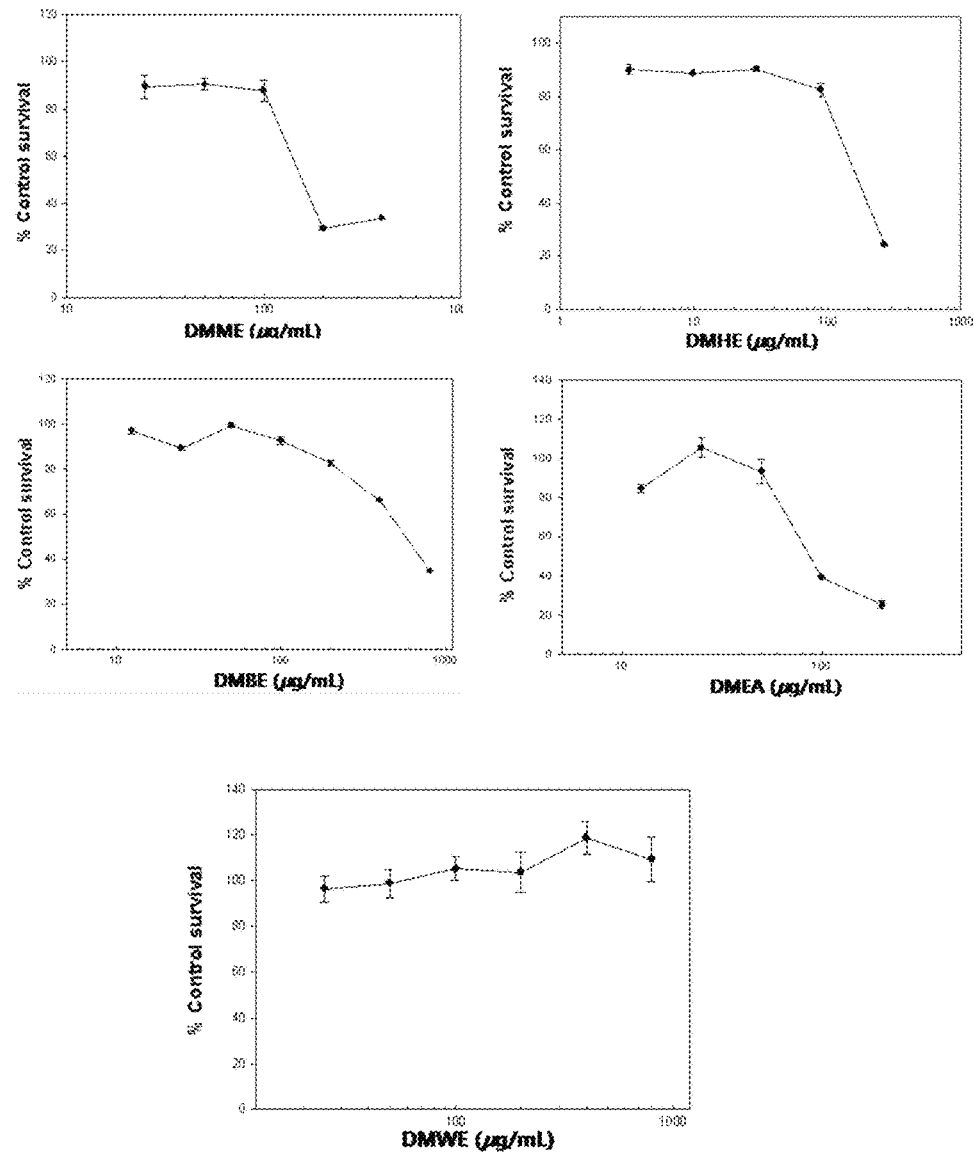
FIG. 10 is a graph illustrating the cytotoxicity assessment of a *Dendropanax morbifera* extract in LNCaP•FGC cells by MTT assay.

As listed in the above-described Table, IC$_{50}$ of hexane, ethyl acetate, methanol and water extract of *Dendropanax morbifera* (DMHE, DMEA, DMME, DMWE) were determined to be 39.86 μg/mL to higher than 1000 μg/mL (FIG. 9.) in HaCaT cells, 88 μg/mL to higher than 800 μg/mL (FIG. 10.) in LNCaP•FGC cells (FIG. 10). In other words, the hydrophobic extracts have shown relatively higher toxicity, but not as much as to be fatal for the cell viability.

Example 4

Quantitative Analysis of Protein and Detection of PGE$_2$ Secretion

COX and microsome PGE synthase-1 (mPGEX-1)-originated PGE$_2$ are considered as important regulators of pulmonary function. Particularly, PGE$_2$ formation on the infection site regulates immune and inflammatory reaction and it was reported that it is disengaged from epidermal cells, once infection occurs (N'Guessan et al., 2007).

Protein concentration was measured using Bio-Rad protein assay based on Bradford (Schleicher and Wieland, 1978). Standard curve was drawn by serial dilution of BSA (bovine serum albumin) and Bio-Rad protein assay reagent was diluted in 1:4 ratios in water. 4 μL of standards and samples were added to 1 mL of diluted staining reagent and measured the absorbance at 595 nm Protein concentration of sample was determined from standard curve made by BSA.

Meanwhile, in order to investigate the secretion of PGE$_2$, HaCaT cells and A549 cells were seeded on 6-well culture plates (5×10$^5$ cells/well) in FBS and antibiotic containing DMEM and RPMI medium, respectively in 5% CO$_2$ humidified incubator at 37° C. and 15-PGDH inhibitors with varying concentrations were treated and supernatant was collected at specific time after the treatment. Using PGE$_2$ enzyme immunoassay kit (Thermo Scientific, Rockford, Ill., USA), the level of intracellular and extracellular PGE$_2$ were measured.

Figure 11:
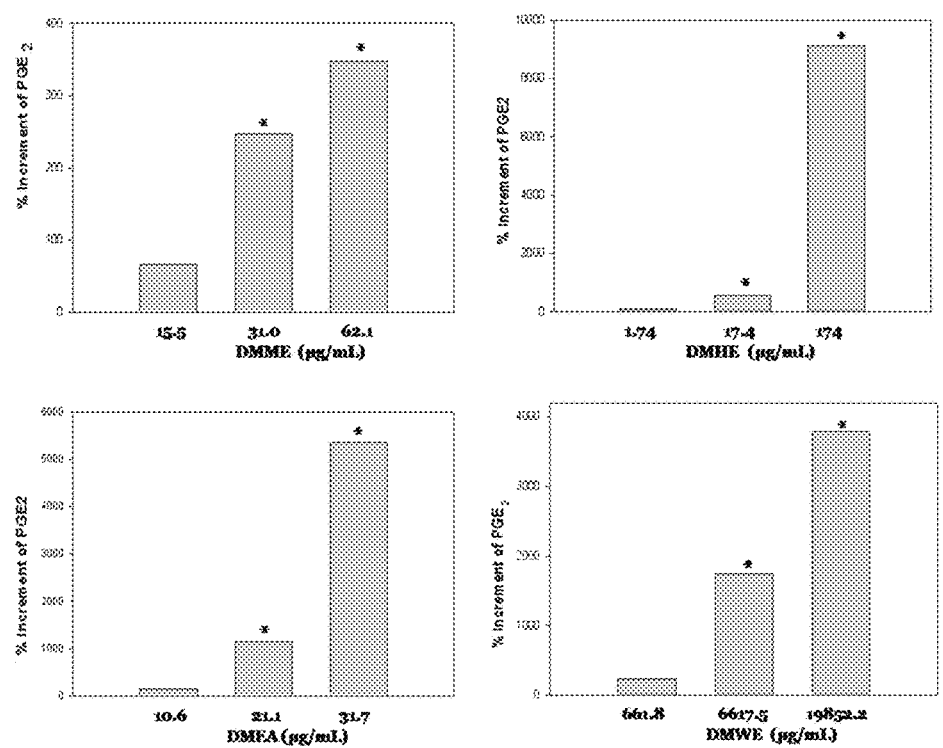
FIG. 11 is a graph illustrating the effect of concentration-dependent increase of $PGE_2$ by a *Dendropanax morbifera* extract in A549 cells.

As the result illustrated in FIG. 11, DMEA (1-, 2-, and 3 fold ED$_{50}$), DMW (1-, 10-, and 100-fold ED$_{50}$), DMHE (1-, 10-, and 100-fold ED$_{50}$) and DMME (0.5-, 1- and 2-fold ED$_{50}$) increased the PGE$_2$ in concentration-dependent manner. *D. morbifera* hexane extract (DMHE) inhibited 15-PGDH more efficiently.

Figure 12:
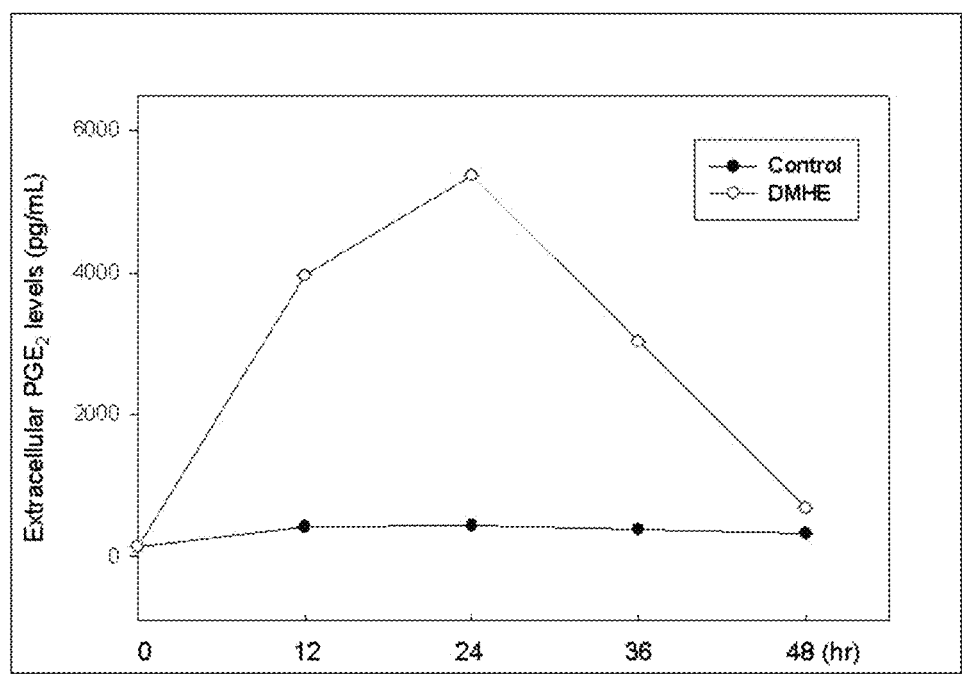
FIG. 12 is a graph illustrating the time-dependent change in extracellular level of $PGE_2$ in HaCaT cells by DMHE of a *Dendropanax morbifera* extract.
Figure 13:
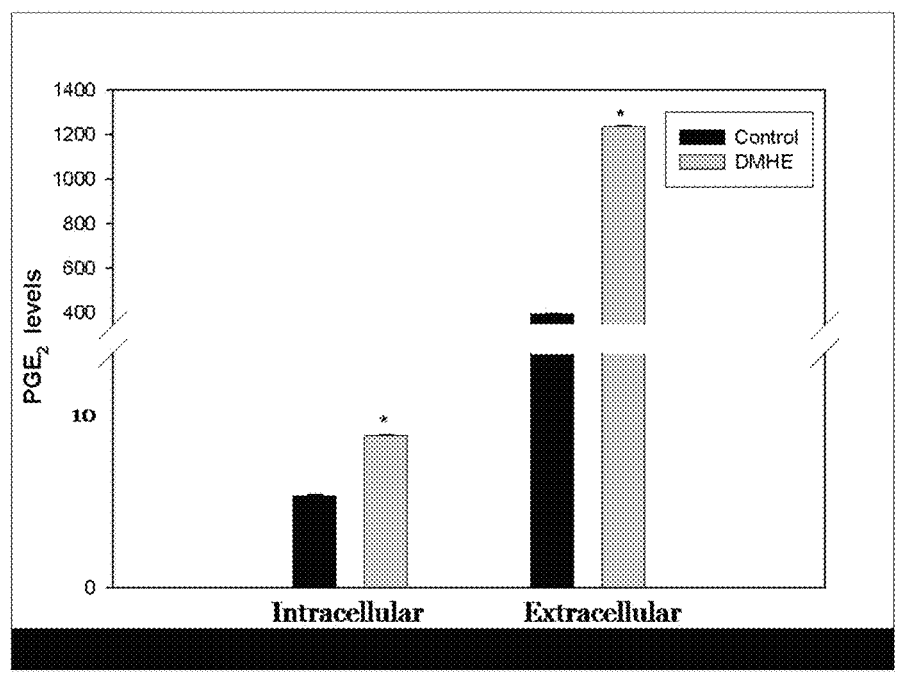
FIG. 13 is a graph illustrating the changes in intracellular and extracellular level of $PGE_2$ in HaCaT cells by hexane extract of *Dendropanax morbifera* extract (DMEM).

And then, time-dependent change of extracellular PGE$_2$ was identified. The level of PGE$_2$ dramatically increased to 1200% of control group when 24 hours were passed and after then, rapidly decreased (Table 4 and FIG. 12). From these results, the appropriate time at which PGE$_2$ should be detected was determined to be 12 hours and by treating DMHE (17.4 μg/mL) for 12 hours and measuring intracellular and extracellular level of PGE$_2$ in the same way, it was confirmed that each level increased to 165% and 315% of the control group, respectively (Table 5 and FIG. 13).

TABLE 4

| Time | Sample | PGE$_2$ (pg/mL) |
|---|---|---|
| 0 hour | Control group | 143.6 |
| | DMHE | 143.6 |
| 12 hour | Control group | 420.4 |
| | DMHE | 3967.1 |
| 24 hour | Control group | 442.9 |
| | DMHE | 5373.2 |
| 48 hour | Control group | 323.3 |
| | DMHE | 687.3 |

TABLE 5

| Sample | Intracellular (ng/mg) (mean ± SD) | Extracellular (pg/mL) (mean ± SD) |
|---|---|---|
| Control group | 1.96 ± 0.18 | 393.67 ± 12.46 |
| DMHE (17.4 μg/mL) | 3.24 ± 0.53* | 1238.04 ± 91.76* |

*p < 0.05

Example 5

Quantitative RT-PCR Analysis

Intracellular and extracellular level of PGE$_2$ is functionally related to the expression level of COX-1/2, MRP4, 15-PGDH and PGT. In order to investigate the effect of *D. morbifera* on the genes above, mRNA expression of COX-1/2, MRP4 and PGT in HaCaT cells was measured after being treated with DMHE (17.4 μg/mL). The concentration of DMHE (17.4 μg/mL, 10× ED$_{50}$) used in the analysis was the concentration determined by previous experiment that was not cytotoxic and sufficiently inhibit the activity of 15-PGDH.

Using TRI reagent (RNAiso Plus, takara), RNA of the entire cells were isolated from the cells. From each RNA sample, 20 μL of cDNA was synthesized (Invitrogen, USA). For PCR reaction, 4 μL or 1:5 diluted cDNA, 4 mM MgCl$_2$, 10 pmole of each primer and 4 μL or Fast Starter Mix buffer (dNTPs, SYBR Green dye and Taq polymerase) were included. Primers used and conditions for RT-PCR is provided in the following Table. For 5R 1, 2 primers that are not listed in Table, certified ones were purchased from Qiagen Korea Ltd. (Seoul, Korea) and each amplicon size was 185 bp, 119 bp and annealing was conducted at 60° C. for 5 seconds and extension was conducted at 72° C. for 8 seconds.

TABLE 6

| Gene | Amplicon (bp) | Primer | | |
|---|---|---|---|---|
| PGT | 386 | Sense | 5'-GGATGCTGTTTGGAGGAATC-3' | (SEQ ID NO: 1) |
| | | Antisense | 5'-GCACGATCCTGTCTTTGCTGA-3' | (SEQ ID NO: 2) |

TABLE 6-continued

| Gene | Amplicon (bp) | Primer | | |
|------|---------------|--------|---|---|
| MRP4 | 394 | Sense | 5'-ACCTCTAACCGACATTCCTG-3' | (SEQ ID NO: 3) |
|      |     | Antisense | 5'-TCAACATATTACAGCCACCAT-3' | (SEQ ID NO: 4) |
| COX-1 | 207 | Sense | 5'-CCTCATGTTTGCCTTCTTTGC-3' | (SEQ ID NO: 5) |
|       |     | Antisense | 5'-GGCGGGTACATTTCTCCATC-3 | (SEQ ID NO: 6) |
| COX-2 | 171 | Sense | 5'-GATCTACCCTCCTCAA-3' | (SEQ ID NO: 7) |
|       |     | Antisense | 5'-GAACAACTGCTCATCAC-3' | (SEQ ID NO: 8) |
| PSA | 217 | Sense | 5'-CCTCCTGAAGAATCGATTCC-3' | (SEQ ID NO: 9) |
|     |     | Antisense | 5'-GAGGTCCAACACTGAAG-3' | (SEQ ID NO: 10) |
| 15-PGDH | 105 | Sense | 5'-TGCTTCAAAGCATGGCATAG-3' | (SEQ ID NO: 11) |
|         |     | Antisense | 5'-AACAAAGCCTGGACAAATGG-3' | (SEQ ID NO: 12) |
| β-actin | 504 | Sense | 5'-GACTATGACTTAGTTGCGTT-3' | (SEQ ID NO: 13) |
|         |     | Antisense | 5'-GTTGAACTCTACATACTTCCG-3' | (SEQ ID NO: 14) |

TABLE 7

| Gene | Hot start | Denaturation | Annealing | Extension |
|------|-----------|--------------|-----------|-----------|
| PGT | | | 60° C., 5 sec | 72° C., 12 sec |
| MRP4 | | | 57° C., 5 sec | 72° C., 16 sec |
| COX-1 | 95° C., 1 min | 95° C., 15 sec | 60° C., 5 sec | 72° C., 15 sec |
| COX-2 | | | 59° C., 5 sec | 72° C., 7 sec |
| PSA | | | 57° C., 5 sec | 72° C., 9 sec |
| 15-PGDH | | | 60° C., 5 sec | 72° C., 5 sec |
| β-actin | | | 55° C., 5 sec | 72° C., 21 sec |

Figure 14:
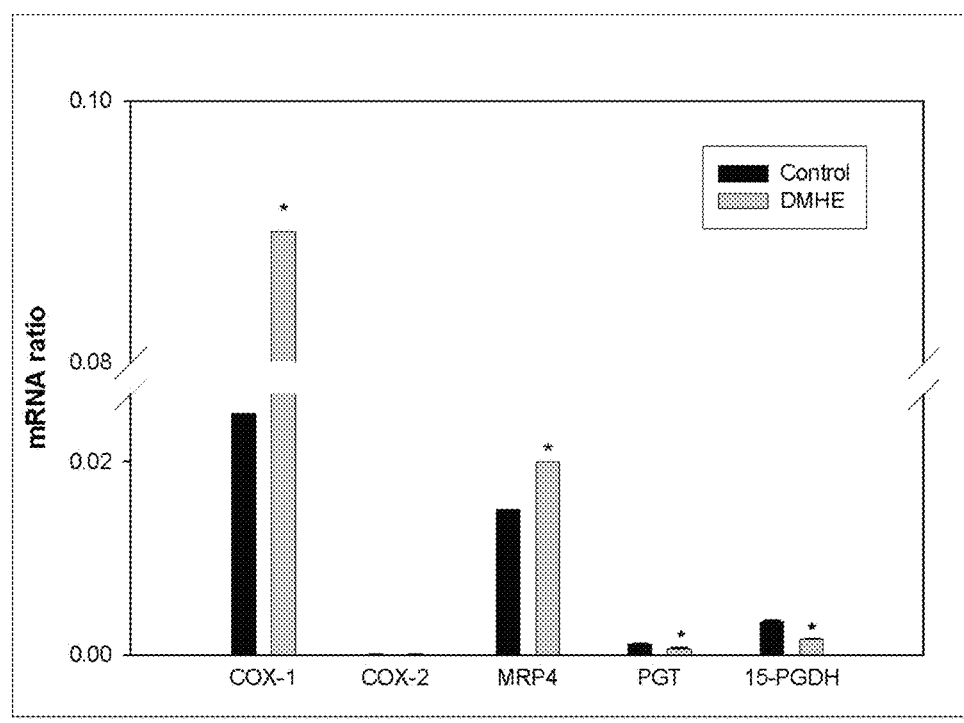
FIG. 14 is a graph illustrating the effect of DMHE on the mRNA expressions of COX-1/2, MRP4, 15-PGDH and PGT in HaCaT cells.

As the result illustrated in FIG. 14, Real-time PCR analysis result indicated that DMH increases the mRNA expression of COX-1 and MRP4, and decreases the expression of PGT and 15-PGDH.

Example 6

In vitro Scratch Analysis

For in vitro scratch analysis (Hintermann et al., 2001; Koivisto et al., 2006), HaCaT cells were seeded $3 \times 10^5$ cells per well on 6-well plates and cultured until 80% confluence was reached. Then, culture medium was replaced with serum-free medium containing mitomycin (10 μg/mL) and cells were cultured for 2 hours to block the proliferation of wound and washed with PBS. Scratch was made by sterilized 200 μL pipette tip and washed again.

The experiment was designed by group treated with non-drug as a negative control, group treated with TGF-β1 (100 pg/mL) as a positive control, and group treated only with DMHE (17.4 μg/mL), and group treated with COX-1 inhibitor (SC 560, 0.5 μM), COX-2 inhibitor (celecoxib, 0.5 μM) and non-selective COX inhibitor (naproxen, 80 μM).

The process of wound healing was observed by taking photographs of identical spots before and after the culture. Experiment was repeated for 3 times and representative photos were illustrated Immediately after the formation of scratch, photos of scratch were taken by microscope (×100) and 48 hours after the culture, photos were taken once more. By measuring the distance between scratch, the % recovery rate by drug was calculated in comparison with the negative control group.

Figure 15:
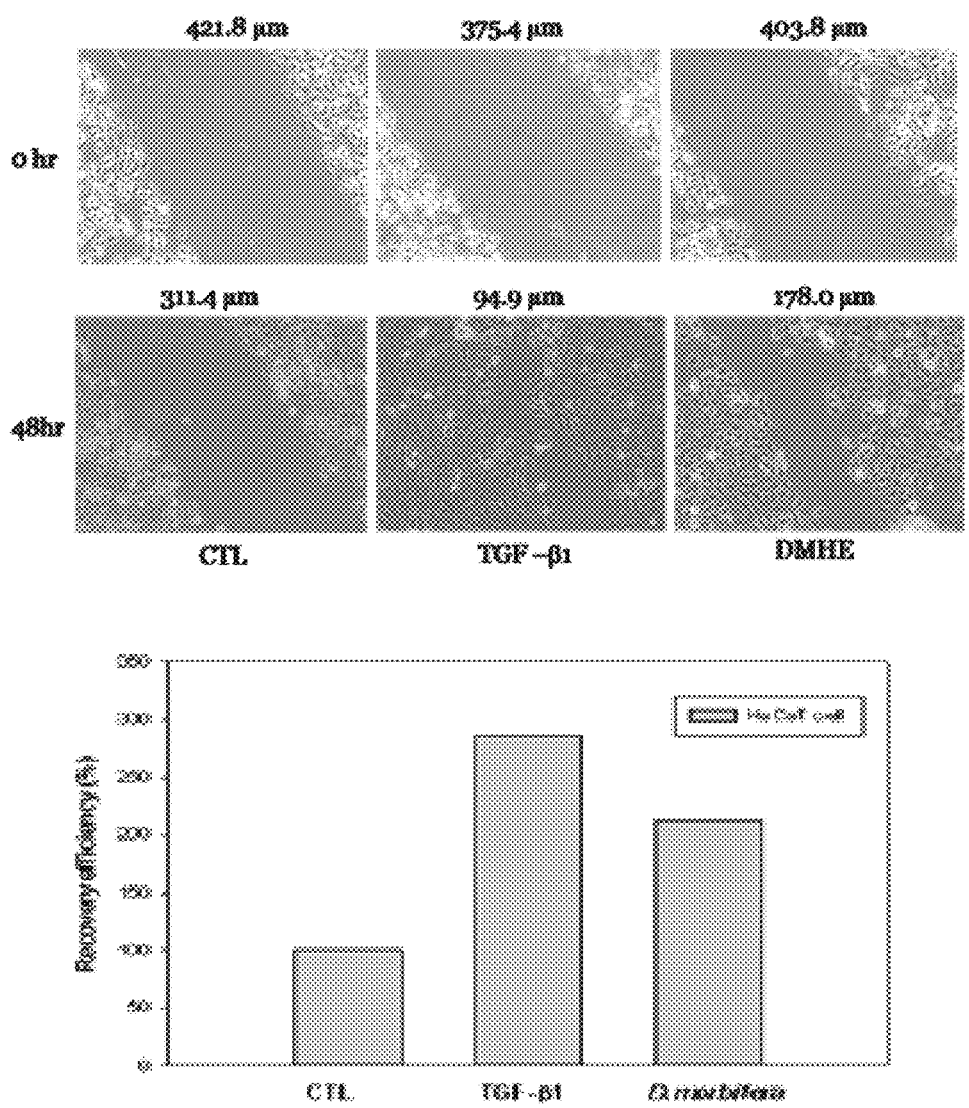
FIG. 15 is a graph and a photograph illustrating the $PGE_2$-mediated wound healing effect of DMHE in HaCaT cells.

As the result illustrated in FIG. 15, in comparison with the negative control group, DMHE promoted the wound healing. This was comparable to the result of TGF-β1. While TGF-β1 showed 253% recovery, DMHE showed 204% recovery.

Figure 16:
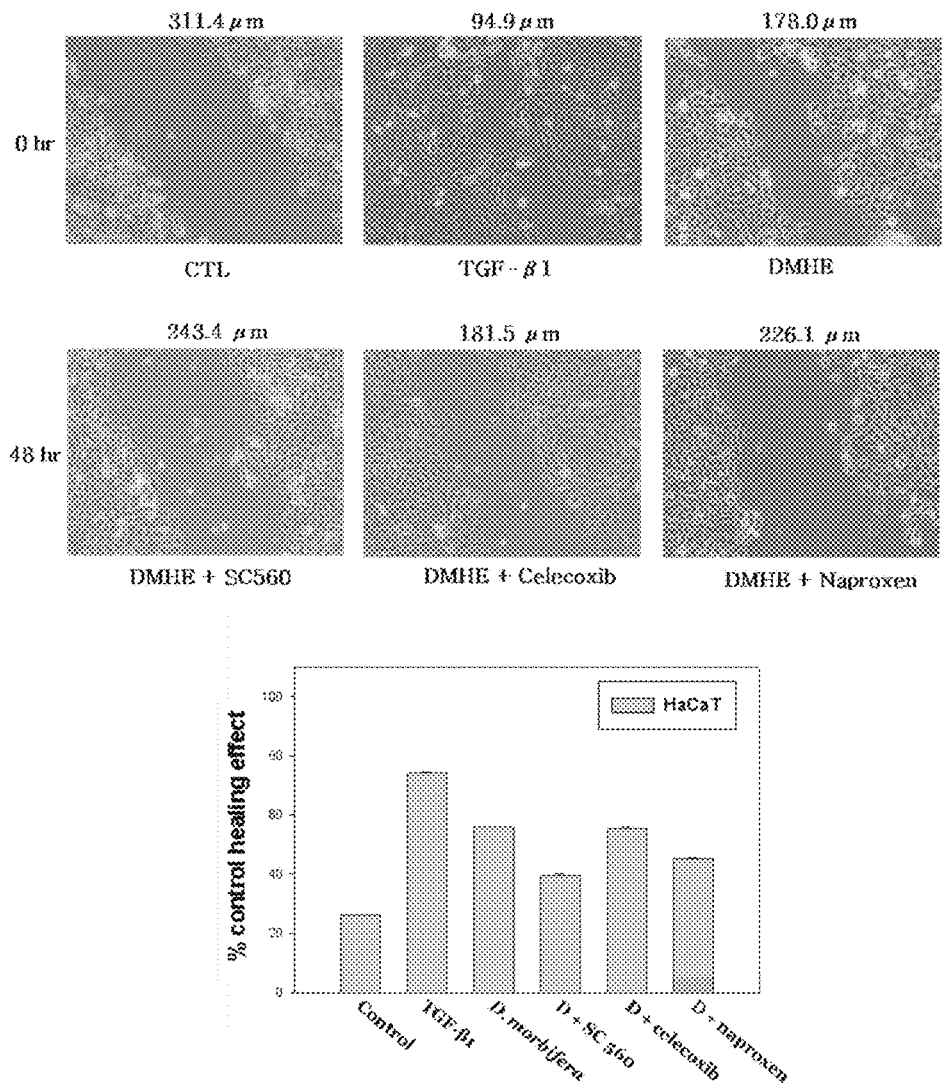
FIG. 16 is a graph and a photograph illustrating the wound healing effect of DMHE in HaCaT cells in the presence or absence of COX-1/2 inhibitor.

Furthermore, as it is illustrated in FIG. 16, the wound healing effect of DMHE is suppressed in the presence of COX inhibitor. Particularly, COX-1 inhibitor (SC560) and non-selective COX inhibitor (naproxen) suppressed wound healing more than COX-2 inhibitor.

These results indicate that COX-1 has greater contribution to increase of $PGE_2$ and wound healing effect of DMHE than COX-2 (FIG. 16). In addition, it corresponds to the gene expression profile of mRNA that is affected by DMHE (FIG. 14).

In the meantime, in order to investigate whether $PGE_2$ is directly involved in scratch healing, 15-PGDH and its coenzyme $NAD^+$ were treated in identical model system.

Figure 17:
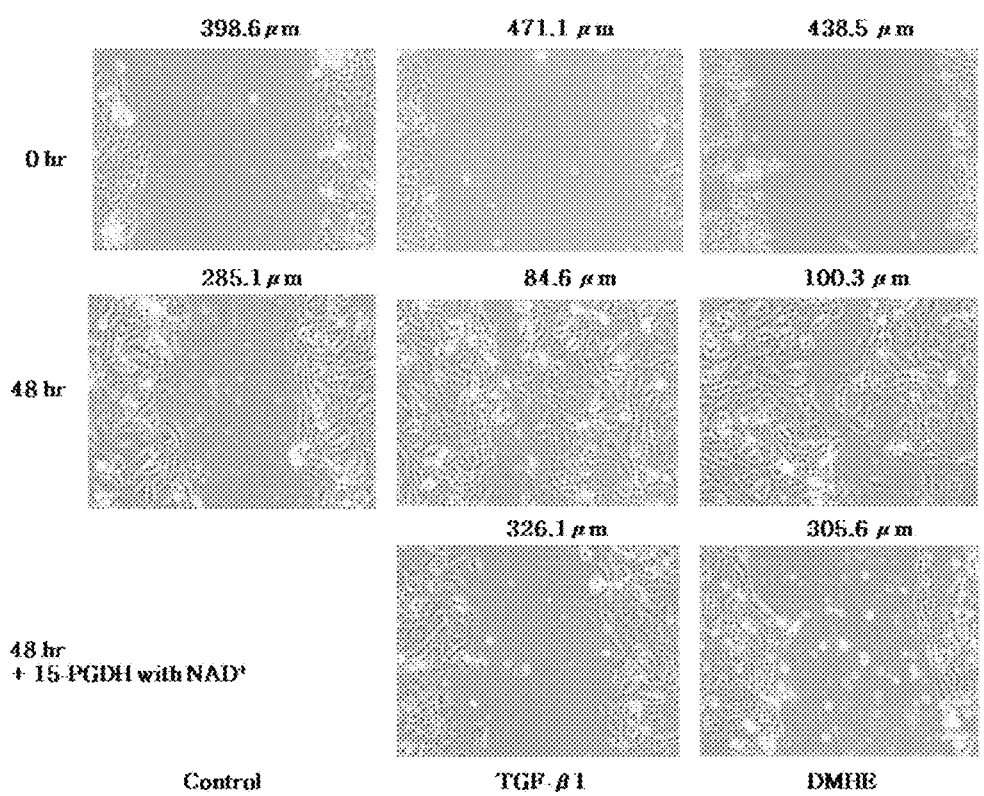
FIG. 17 is a photograph illustrating the wound healing effect of DMHE in HaCaT cells in the presence or absence of 15-PGDH or $NAD^+$.

As the result illustrated in FIG. 17, treatment with 15-PGDH and $NAD^+$ made wound healing effect of DMHE and TGF-β1 completely vanished and this means that $PGE_2$ is directly involved in wound healing.

Example 7

In vivo Gastric Ulcer Prevention Effect

To investigate the prevention effect of *Dendropanax morbifera* for gastric ulcer, 3 week old male ICR mice with weight of 20±2 g were used. The mice above were purchased from Damul Science Co. (Daejuen, Korea). Animal experiments conducted in the examples were approved by Chonnam National University animal experiment ethics committee (IRB) (CNU IACUC-YB-R-2012-11).

The above-described animals were divided into 3 groups (for each group, n=7) that comprise normal group (vehicle 0.5% CMC (carboxyl methylcellulose)), positive control group (sucralfate, 100 mg/kg in 0.5% CMC) and experimental group (*Dendropanax morbifera* leaf hexane extract in 0.5% CMC).

Balanced diet was provided to the animals and they were allowed to drink water freely. One week later, animals were forced to fast for all day long. 24 hours before inducing the intestinal bleeding, *Dendropanax morbifera* hexane extract (DMHE, dissolved in 0.5% CMC) was administered with oral dose of 0.87 mg/kg and administered once more 1 hour before HCl/ethanol was applied. It was conducted for the negative (0.5% CMC, 1 mL/kg) and positive control group (sucralfate, 100 mg/kg in 0.5% CMC) simultaneously. By administering HCl/ethanol mixture containing 150 mM HCl in 60% ethanol into stomach, gastric lesion of hemorrhage was induced. One hour after ethanol administration, animals above were sacrificed by dislocation of the cervical spine and stomach was rapidly removed. After being rinsed with water, it was laid on paraffin plate and photographed.

Figure 18:
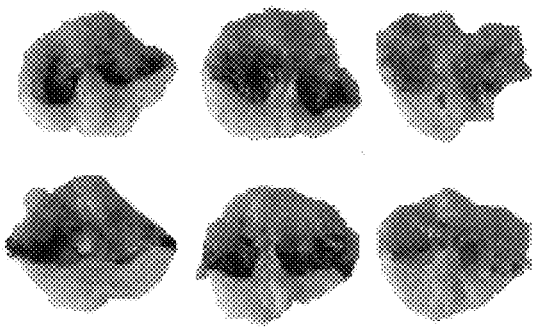
FIG. 18 is a photograph illustrating the gastric ulcer preventive effect of DMHE in ICR mice.
Figure 18:
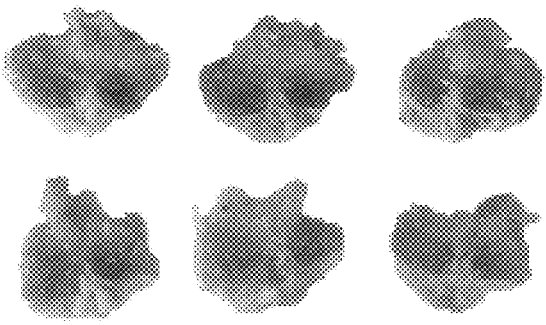
Figure 18:
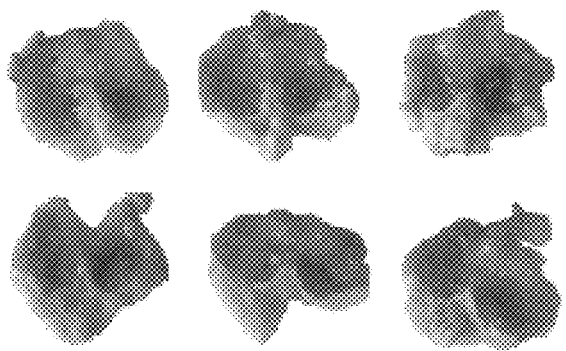

The results are illustrated in FIG. 18.

While the negative control group (no drugs were treated) have shown a great amount of bleeding and edema, group treated with DMHE (0.87 mg/kg) and the positive sucralfate-treated group (100 mg/kg) have not shown any type of lesion.

Example 8

In vivo Wound Healing Effect

To confirm the wound healing effect of *Dendropanax morbifera* extract of the present invention in vivo, following experiments were conducted. First, 7 week old male ICR mice (average weight: 25 g) were purchased from Damul Science Co. (Daejuen, Korea) and after a week of adjustment period, they were anesthetized by administering anesthetic (zoletil, 50 μL) into the abdominal cavity and then circular wound with diameter of 5 mm was made under anesthesia. From a day later, being divided into 4 groups, wound of each group was treated with drugs daily basis as below while 10 μL of drugs were applied to wound of each group and the degree of healing was observed by tissue staining Animal experiments conducted in the examples were approved by Chonnam National University animal experiment ethics committee (IRB) (CNU IACUC-YB-R-2012-12) and tissue staining was done by fragmenting the wounded tissue of mice on which the above experiment of 4 groups was conducted and stained with hemtoxylin-Eosin (H & E). The distance of recovered wound was measured by visualizing stained tissues with microscope (40×). Moreover, the wound healing efficiency was calculated based on the distance measured.

TABLE 8

| Group | Drug treated | Marks in FIG. |
|---|---|---|
| 1 | Vehicle (Control group) | A1 |
| 2 | TGF-beta1 (20 ng/day), Positive control group | A2 |

TABLE 8-continued

| Group | Drug treated | Marks in FIG. |
|---|---|---|
| 3 | DMHE (16.5 ug/day, *Dendropanax morbifera* hexane extract) | A3 |
| 4 | DMHE (66 ug/day, *Dendropanax morbifera* hexane extract) | A4 |

Figure 19:
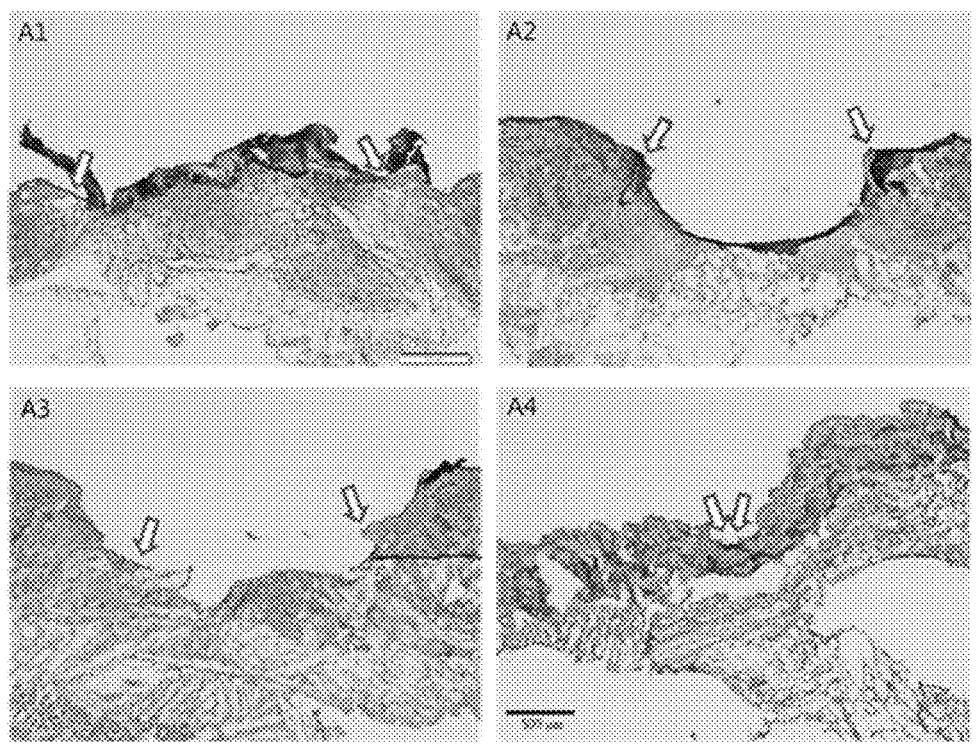
FIG. 19 is a photograph that the degree of wound healing on mice model with circular wound, each of which were treated with 0.1% BSA (control group), TGF-β1 (20 ng/day), DMHE (16.5 μg/day, a *Dendropanax morbifera* hexane extract), and DMHE (66 μg/day, a *Dendropanax morbifera* hexane extract) were observed by a tissue staining.
Figure 20:
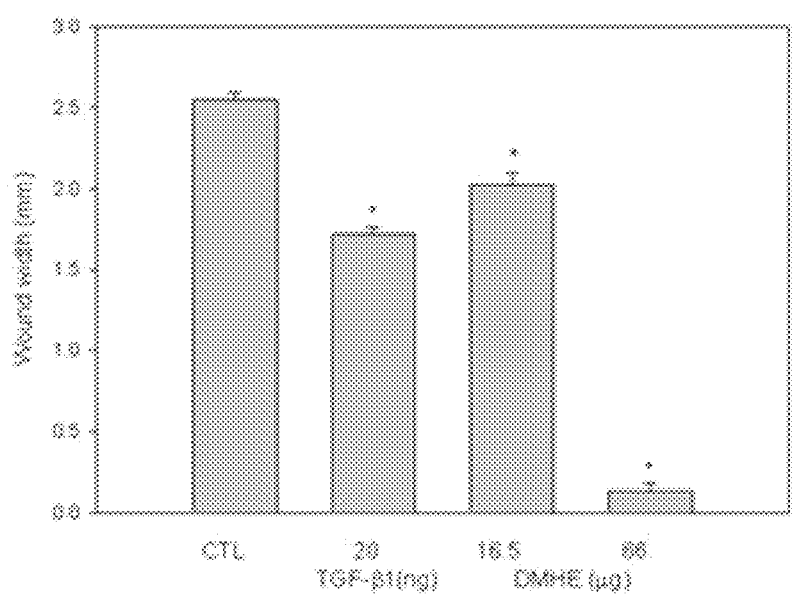
FIG. 20 is a graph illustrating the distance between wounds determined by measuring the distance between two spots on two arrows of FIG. 19.
Figure 21:
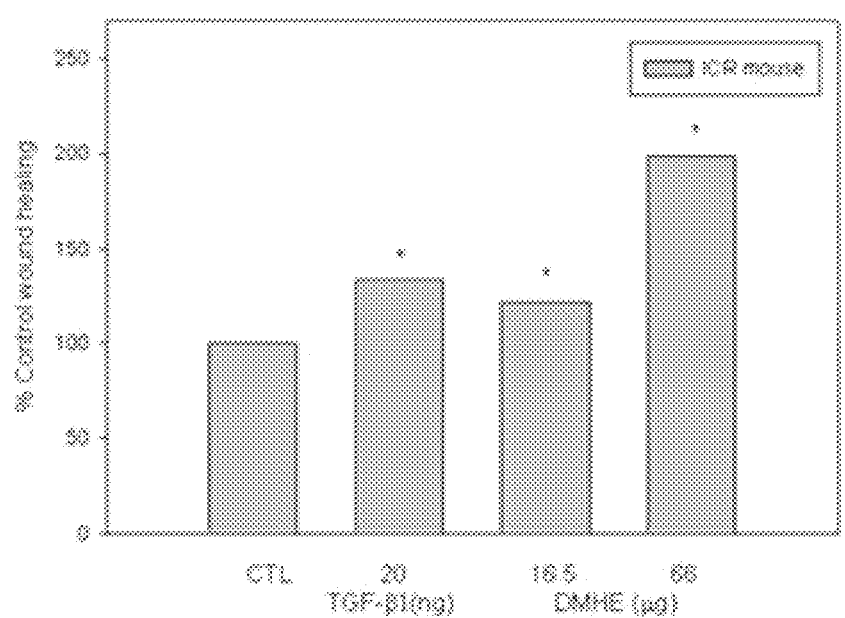
FIG. 21 is a graph illustrating the wound healing efficacy calculated by comparing the distance measured in FIG. 20 with that of the control group.

As a result of the analysis, wound healing effect of experimental groups determined by tissue staining was, as illustrated in FIG. 19, the group treated with the *Dendropanax morbifera* extract of the present invention (A3 & A4) have shown shortened distances between wound compared to those of the other groups (arrows in figure mark the point at which the reepithelialization of epithelial cells is terminated during the wound healing), and that is, the distance measured between the points on two arrows marked in each of figures of FIG. 19 was illustrated in FIG. 20, and the healing efficiency calculated by comparing the measured distances to those of the control group was illustrated in FIG. 21.

More specifically, as it is illustrated in FIG. 20, the distance between wound measured for the control group on the $4^{th}$ day after the drug treatment was 2.55 mm, which means approximately 49% was healed if compared to the diameter (5 mm) of initially created wound, and for TGF-β1 group, the group of positive control, the distance was 1.72 mm, which corresponds to 65.6% of healing. In addition, it was 2.02 mm with 59.5% of healing when 16.5 μg of *Dendropanax morbifera* hexane extract of the present invention (DMHE) was treated and 0.13 mm with 97.4% power of healing when 66 μg was treated.

Particularly, for group treated with DMHE (66 μg), healing efficacy was 198% of the negative control group and 148% of the positive control group, which suggests that the *Dendropanax morbifera* extract of the present invention can be used as a very useful wound healing agent.

Hitherto, the present invention was addressed mainly by the favorable exemplary embodiments thereof. An ordinary skill in the art to which the present invention belongs will understand that the present invention can be transformed and implemented without deviating from the essential properties thereof. Thus, all exemplary embodiments disclosed herein should be considered not in terms of limited aspects but in terms of descriptive aspects. The scope of the present invention is not shown in the aforementioned description, but in the scope of request for a patent and all discrepancies existing in the equivalent scope should be regarded as included in the present invention.

The invention claimed is:

1. A method for treating a condition associated with activity of 15-PGDH (15-Hydroxyprostaglandin Dehydrogenase) or prostaglandin $E_2$ ($PGE_2$), the method comprising orally administering *Dendropanax morbifera* leaf extract to a subject in need thereof, wherein the condition is peptic ulcer or gastritis.

2. The method of claim 1, wherein the *Dendropanax morbifera* extract is a crude extract of *Dendropanax morbifera* Lev., a polar solvent soluble extract, or a non-polar solvent soluble extract.

3. The method of claim 2, wherein the crude extract is obtained by using a solvent selected from the group consisting of water including purified water, methanol, ethanol, butanol or a mixed solvent thereof.

4. The method of claim 2, wherein the polar solvent soluble extract is obtained by using a solvent selected from the group consisting of water, ethanol, butanol or a mixed solvent thereof.

5. The method of claim 2, wherein the non-polar solvent soluble extract is obtained by using hexane, chloroform, dichloromethane, or ethyl acetate.

6. The method of claim 1, wherein the *Dendropanax morbifera* extract has effects on:
    (i) inhibition of enzymatic activity of 15-PGDH;
    (ii) intracellular and extracelluar increases of $PGE_2$;
    (iii) increase in gene expression of COX-1 (cyclooxygenase-1) and MRP4 (multidrug resistance-associated protein 4);
    (iv) inhibition of PGT (prostaglandin transporter) expression; and
    (v) inhibition of 5α reductase expression.

* * * * *